(12) United States Patent
    Blatchford et al.

(10) Patent No.: US 11,376,379 B2
(45) Date of Patent: Jul. 5, 2022

(54) FLOW GOVERNOR ASSEMBLIES FOR USE IN MEDICINAL INHALERS

(71) Applicant: KINDEVA DRUG DELIVERY L.P., St. Paul, MN (US)

(72) Inventors: Christopher G. Blatchford, Loughborough (GB); Romain U. G. Guion, Cambridge (GB); Christopher B. J. Groombridge, Stevenage (GB); Simon L. Calcutt, Cambridge (GB)

(73) Assignee: Kindeva Drug Delivery L.P., St. Paul, MN (US)

( * ) Notice: Subject to any disclaimer, the term of this patent is extended or adjusted under 35 U.S.C. 154(b) by 575 days.

(21) Appl. No.: 16/064,421

(22) PCT Filed: Dec. 13, 2016

(86) PCT No.: PCT/US2016/066305
    § 371 (c)(1),
    (2) Date: Jun. 20, 2018

(87) PCT Pub. No.: WO2017/112452
    PCT Pub. Date: Jun. 29, 2017

(65) Prior Publication Data
    US 2018/0369512 A1    Dec. 27, 2018

Related U.S. Application Data

(60) Provisional application No. 62/270,076, filed on Dec. 21, 2015, provisional application No. 62/289,663, filed on Feb. 1, 2016.

(51) Int. Cl.
    *A61M 15/00*    (2006.01)
    *A61M 16/00*    (2006.01)

(52) U.S. Cl.
    CPC ........ *A61M 15/002* (2014.02); *A61M 15/009* (2013.01); *A61M 15/0091* (2013.01);
    (Continued)

(58) Field of Classification Search
    CPC ........ A61M 15/002; A61M 2205/3334; A61M 15/009; A61M 15/0091;
    (Continued)

(56) References Cited

U.S. PATENT DOCUMENTS 5,161,524 A    11/1992 Evans
5,217,004 A    6/1993 Blasnik et al.
(Continued)

FOREIGN PATENT DOCUMENTS

DE    199 12 461    9/2000
DE    101 26 807    12/2002
(Continued)

OTHER PUBLICATIONS

Levy, M.L. et al.; "Asthma patients' inability to use a pressurised metered-dose inhaler (pMDI) correctly correlates with poor asthma control as defined by the Global Initiative for Asthma (GINA) strategy: a retrospective analysis"; Primary Care Respiratory Journal; vol. 22, No. 4; 2013; pp. 406-411.
(Continued)

*Primary Examiner* — Victoria Murphy
(74) *Attorney, Agent, or Firm* — Mueting Raasch Group

(57) ABSTRACT

A flow governor assembly for use with a medicinal inhaler. The assembly can include a housing that defines an air flow path; a flow governor positioned in the air flow path to govern air flow in the air flow path to a target governing volumetric flow rate; and a constriction in the air flow path. The flow governor can be configured to provide a variable, or dynamic, resistance to air flow in the air flow path as a function of air pressure drop between an inlet and an outlet (Continued)

of the flow governor. The constriction can be configured to provide a fixed, or static, resistance to air flow in the air flow path.

18 Claims, 19 Drawing Sheets

(52) U.S. Cl.
CPC ............... *A61M 2016/0018* (2013.01); *A61M 2016/0027* (2013.01); *A61M 2205/3331* (2013.01); *A61M 2205/3334* (2013.01); *A61M 2205/3341* (2013.01); *A61M 2205/50* (2013.01); *A61M 2205/8206* (2013.01)

(58) Field of Classification Search
CPC .. A61M 2016/0018; A61M 2016/0027; A61M 2205/3331; A61M 2205/3341
See application file for complete search history.

(56) References Cited

U.S. PATENT DOCUMENTS

| | | | |
|---|---|---|---|
| 5,347,998 A | 9/1994 | Hodson et al. | |
| 5,392,768 A | 2/1995 | Johannsson et al. | |
| 5,437,271 A | 8/1995 | Hodson et al. | |
| 5,617,844 A | 4/1997 | King | |
| 5,655,520 A | 8/1997 | Howe et al. | |
| 5,692,492 A | 12/1997 | Bruna et al. | |
| 5,839,430 A * | 11/1998 | Cama | A61B 5/411 128/200.14 |
| 5,941,240 A | 8/1999 | Gonda et al. | |
| 6,070,573 A | 6/2000 | Howe et al. | |
| 6,109,261 A | 8/2000 | Clarke et al. | |
| 6,176,237 B1 | 1/2001 | Wunderlich et al. | |
| 6,260,549 B1 | 7/2001 | Sosiak | |
| 6,357,442 B1 | 3/2002 | Casper et al. | |
| 6,651,651 B1 * | 11/2003 | Bonney | A61M 15/009 128/200.23 |
| 6,655,379 B2 | 12/2003 | Clark et al. | |
| 6,681,762 B1 | 1/2004 | Scheuch et al. | |
| 6,904,907 B2 | 6/2005 | Speldrich et al. | |
| 7,073,499 B1 | 7/2006 | Reinhold et al. | |
| 7,296,567 B2 | 11/2007 | Mahon et al. | |
| 7,891,358 B2 | 2/2011 | Kolb et al. | |
| 8,684,002 B2 | 4/2014 | Huber et al. | |
| 8,944,050 B2 | 2/2015 | Hyun et al. | |
| 2006/0137681 A1 | 6/2006 | Von Hollen et al. | |
| 2008/0017197 A1 * | 1/2008 | Kaneko | A61M 11/00 128/203.12 |
| 2008/0066741 A1 * | 3/2008 | LeMahieu | A61M 15/00 128/200.21 |
| 2009/0314372 A1 | 12/2009 | Ruskewicz et al. | |
| 2013/0298907 A1 | 11/2013 | Zuyderhoudt | |
| 2014/0352690 A1 | 12/2014 | Kolb et al. | |

FOREIGN PATENT DOCUMENTS

| | | |
|---|---|---|
| EP | 0 050 654 | 5/1982 |
| EP | 0 808 635 | 11/1997 |
| EP | 0 895 788 | 2/1999 |
| EP | 0 965 355 | 12/1999 |
| EP | 1 036 569 | 9/2000 |
| EP | 1 163 921 | 12/2001 |
| EP | 1 399 210 | 3/2004 |
| GB | 2 104 393 | 3/1983 |
| GB | 2 266 466 | 11/1993 |
| JP | 07509378 | 10/1995 |
| KR | 20150025353 | 3/2015 |
| TL | WO 1995/05208 | 2/1995 |
| WO | WO 1992/12799 | 8/1992 |
| WO | 1993012823 | 7/1993 |
| WO | WO 1998/41253 | 9/1998 |
| WO | WO 1999/06091 | 2/1999 |
| WO | WO 1999/47196 | 9/1999 |
| WO | WO 2000/16838 | 3/2000 |
| WO | WO 2000/78378 | 12/2000 |
| WO | WO 2001/00263 | 1/2001 |
| WO | WO 2001/34231 | 5/2001 |
| WO | WO 2001/41851 | 6/2001 |
| WO | WO 2001/70313 | 9/2001 |
| WO | WO 2001/70316 | 9/2001 |
| WO | WO 2001/70319 | 9/2001 |
| WO | WO 2001/85245 | 11/2001 |
| WO | WO 2002/24267 | 3/2002 |
| WO | WO 2003/000329 | 1/2003 |
| WO | WO 2003/035155 | 5/2003 |
| WO | WO 2003/055548 | 7/2003 |
| WO | WO 2009/128491 | 10/2009 |
| WO | WO 2015/034709 | 3/2015 |
| WO | WO 2017/112400 | 6/2017 |
| WO | WO 2017/112451 | 6/2017 |
| WO | WO 2017/112476 | 6/2017 |
| WO | WO 2017/112748 | 6/2017 |

OTHER PUBLICATIONS

Japanese Office Action for JP Patent Application No. 2018-550655 dated Apr. 28, 2022; 10 pgs. including English Translation.

* cited by examiner

FLOW GOVERNOR ASSEMBLIES FOR USE IN MEDICINAL INHALERS

CROSS REFERENCE TO RELATED APPLICATIONS

This application is a national stage filing under 35 U.S.C. 371 of PCT/US2016/066305, filed Dec. 13, 2016, which claims the benefit of U.S. Provisional Patent Application No. 62/270,076, filed Dec. 21, 2015 and U.S. Provisional Patent Application No. 62/289,663, filed Feb. 1, 2016, the disclosures of which are incorporated by reference in their entirety herein.

FIELD

The present disclosure generally relates to flow governor assemblies for use in medicinal inhalers, and medicinal inhalers comprising the flow governor assemblies.

BACKGROUND

Delivery of aerosolized medicament to the respiratory tract for the treatment of respiratory and other diseases is conventionally done using inhalers of either the pressurised metered dose inhaler (pMDI), the dry powder inhaler (DPI) or the nebulizer type. pMDI inhalers in particular have become an industry standard, and are familiar to many patients who suffer from either asthma or from chronic obstructive pulmonary disease (COPD). Conventional pMDI devices comprise an aluminum canister, sealed with a metering valve, which contains the medicament formulation. Generally, the medicament formulation is a pressurized formulation containing either fine particles of one or more medicinal compounds suspended in a liquefied hydrofluoroalkane (HFA) propellant, or a solution of one or more medicinal compounds dissolved in a propellant/co-solvent system. Formulations incorporating one drug in solution and another one in suspension form are also known.

In a conventional pulmonary pMDI, the sealed canister is provided to the patient in an actuator. The actuator is conventionally a generally L-shaped plastic molding comprising a generally cylindrical vertical tube that surrounds the canister plus a generally horizontal tube that forms a patient port (e.g., a mouthpiece or nosepiece) that defines an inspiration orifice. To use such an inhaler, the patient exhales, places the patient port in a body cavity (e.g., mouth or nose) and then inhales to draw air through the inspiration orifice. (In the case of nasal pMDIs, it is not always necessary to inhale.) The majority of such inhalers are of the pulmonary "press-and-breathe" type, where the patient must press down on the protruding end of the canister in order to operate the metering valve to release a metered dose of medicament from the canister into the inhaled air stream and thence through the mouthpiece into their lungs. This requires a significant degree of coordination of timing of inhalation and dose release if the emerging cloud of aerosolized medicament is to be taken far enough into the lungs to provide maximum therapeutic benefit. If the patient releases the dose before inspiratory flow has been established, then a proportion of the drug is likely to be lost in the mouthpiece or the patient's mouth. Conversely, if released much after the start of inhalation, then the deeper regions of the lungs might already be full of air and not penetrated by the following bolus of released medicament aerosol.

To overcome what can be quite a challenge for some patients, pMDI device designs have been created that employ automatic breath-actuated triggering, releasing a dose only in response to the patient's inhaled breath. The AUTOHALER™ metered dose inhaler, available from 3M Company, St. Paul, Minn., and the EASIBREATHE™ inhaler, available from Teva Pharmaceutical Industries Ltd., Israel, are two such pMDI devices that use breath-actuation to attempt to better coordinate dose release with inhalation.

SUMMARY

Even though breath-actuated inhalers can be a useful aid in achieving coordination between inhalation and medicament dose release, with consequently improved medicament delivery to many patients' lungs, these devices are however unable to overcome all the potential weaknesses that patients can exhibit in their inhaler use technique. For example, even if patients can achieve good timing of dose release, whether via breath-actuation or simply via good press-and-breathe coordination, they can have a tendency to inhale at suboptimal flow rates. For example, very high inspiratory flow rates (i.e., volumetric flow rates) can give rise to excessive and problematic drug deposition on the back of the throat, while very low inspiratory flow rates can lead to poor entrainment of the aerosolized medicament spray. A related additional potential problem is that very high inspiratory flow rates can lead to more rapid filling of the lungs and consequently an even greater need for good coordination.

As a result of poor inhalation and dose release coordination, many patients do not get the full therapeutic benefit of their medicinal inhalers. For example, many patients with uncontrolled asthma are unable to (i) achieve a flow rate between 10 to 50 liters/minute (L/min.); (ii) maintain the flow rate for at least 1.5 seconds; and (iii) hold their breath for at least 5 seconds after inspiration. Poor inhaler use technique has been found to correlate to poor control of asthma. Similar considerations probably apply to other respiratory diseases treated using inhaled medication, e.g. to COPD.

The general view in the guidance provided by pharmaceutical companies is that pMDI medications should be taken with patients taking a slow and deep inhalation, normally interpreted as being less than 50-60 L/min.

For conventional pMDIs and other inhalers, however, the inhalation flow rate can be poorly controlled from one user to another and even from one breath to another for the same patient. Some patients can sometimes achieve flow rates as high as 250 L/min., while others can sometimes achieve an order of magnitude less. Inhaling the medicament at a lower flow rate tends to reduce drug impaction in the upper airways and increases drug deposition deeper in the lung. If a patient is unable to control their asthma, or any other respiratory disease requiring use of an inhaler, this will impact their quality of life and may lead to the requirement for further medical intervention.

Spacer devices have previously been devised which fit onto the mouthpiece of a pMDI in order to reduce the velocity of the emergent plume of medicament aerosol and to provide a volume in which it can expand and its propellant can evaporate more completely. This serves to avoid some of the problems of coordination and also avoids the tendency for high throat deposition caused by excessively fast drug particle inhalation. However, spacer devices are very bulky, and they can retain an excessive proportion of the drug on their walls, thereby reducing the dose that reaches the patient. Spacer devices can also be highly sensitive to electrostatic charge, which can often be strongly affected by the way in which they are washed or dried.

Because the manner in which patients inhale through their pMDIs is an important determinant of the delivery of drug to their lungs and therefore of the benefits they obtain from their medication, the present inventors sought to control the inhalation profile.

A further difficulty arises in getting all patients to inhale in a similar and consistent manner. Inhaler designs each have their own inherent resistance (R) to air flow. This is often expressed in the units $(Pa)^{0.5}(min./L)$, and is related to inhalation air flow rate (FR) and patient-created pressure drop (PD) by the equation:

$$R=PD^{0.5}/FR.$$

Existing pMDI inhalers usually have low inherent resistances to air flow, for example below 0.5 $Pa^{0.5}$ min./L, which makes it difficult for patients to control their inhalation flowrate. Breathing profiles can be too rapid. Breath-dosing coordination can be difficult under such circumstances, and both the inter-patient and intra-patient variability can be high. With resistances of this order it can also be difficult for patients to achieve a steady flow rate of a duration of more than perhaps 2 to 2.5 seconds. Flow rate consistency during an inspiratory maneuver, and between inhalations, can be difficult to obtain. For example, flow rate 'spikes' can occur, whereby patients achieve fairly high but very transient flow rates. This can lead to poor spatial distributions of drug in their airways.

However, adding a significant fixed ('static') resistance to the design of a pMDI device also poses problems. By restricting the geometry of the air flow path in an inhaler, much higher resistances could be created, for example 1.6 $Pa^{0.5}$ min./L or more. Such resistances are typical of some DPI devices, where a high resistance is required to generate the energy needed to disperse and/or de-agglomerate a dose of medicament powder from a system without the energy content of a liquefied propellant. Unfortunately, though, while high resistances make it much easier for many patients to inhale more slowly and steadily through an inhaler, and for a longer period (e.g. 5 seconds or more), they pose an obstacle to some weaker patients who struggle to inhale adequate amounts of air against such a resistance. COPD patients, in particular, often find it difficult to inhale through such high resistances because of their impaired lung function.

In order to overcome some of the above-described issues related to either a low or a high inhaler resistance, while also avoiding the need for a spacer device, the present inventors developed the flow governors of the present disclosure, which have the ability to change their geometry and resistance to air flow as a function of pressure drop experienced, i.e., between an inlet and outlet of the flow governor. Flow governors of the present disclosure (which can also be referred to as "flow rate limiters," "flow limiters," "flow regulators," "flow limitation devices," or derivations thereof) allow appreciable air flow rates at low differential pressures, while increasing air flow resistance at higher differential pressures in order to limit the air flow rates to values more consistent with those obtained at lower differential pressures to reduce inter-patient and intra-patient inhalation variability.

Some aspects of the present disclosure provide a flow governor assembly for use with a medicinal inhaler. The assembly can include a housing that defines an air flow path including an air inlet and an air outlet. The assembly can further include a flow governor positioned in the air flow path (i.e., positioned in the housing) between the air inlet and the air outlet to govern air flow (e.g., substantially all of the air flow) in the air flow path to a target governing volumetric flow rate. The flow governor can be configured to provide a dynamic resistance to air flow in the air flow path as a function of air pressure drop between an inlet and an outlet of the flow governor. The assembly can further include a constriction in the air flow path (i.e., between the air inlet and the air outlet), the constriction configured to provide a static resistance to air flow in the air flow path. The constriction can be positioned in at least one of (i) a location in the housing upstream of the flow governor and (ii) a location in the housing downstream of the flow governor.

In some aspects of the present disclosure, the flow governor can include (i) a tubular element that defines at least a portion of an air flow path, the tubular element comprising at least one flexible wall configured to flex inwardly in response to an air flow in the air flow path; and (ii) an internal support structure, located within the tubular element and configured to preserve at least a predetermined cross-sectional area of the air flow path within the tubular element when the at least one flexible wall of the tubular element flexes inwardly.

Other features and aspects of the present disclosure will become apparent by consideration of the detailed description and accompanying drawings.

DETAILED DESCRIPTION

Figure 1:
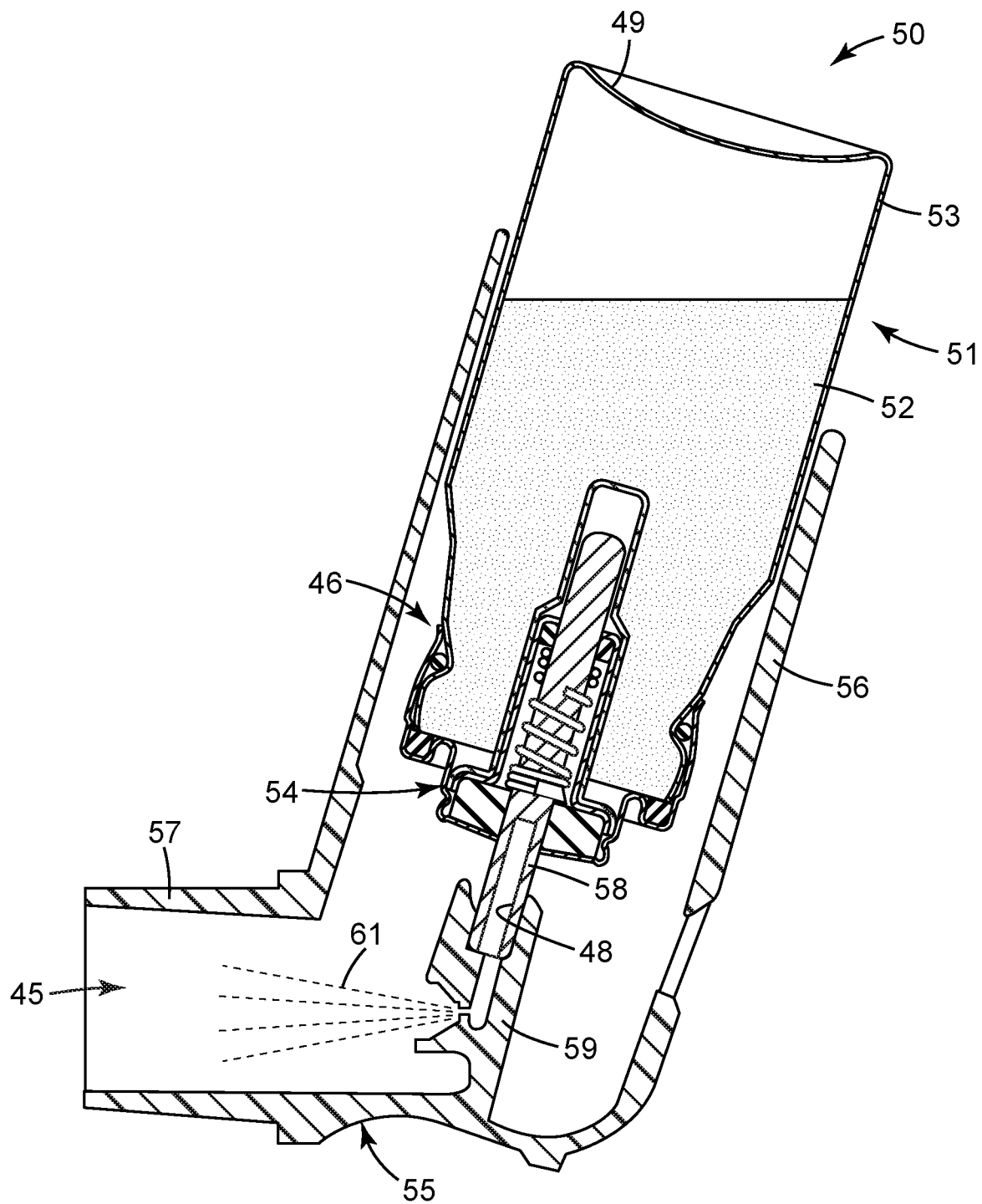
FIG. 1 is a side cross-sectional view of a conventional pressurized metered dose inhaler (pMDI).

The present disclosure generally relates to flow governor assemblies, or medicinal inhalers, comprising a static air flow resistance and a dynamic air flow resistance (e.g., that varies as a function of the pressure drop experienced). The flow governor assemblies can be employed in a medicinal inhaler. In some embodiments, the flow governor assemblies of the present disclosure can include a flow governor to provide the dynamic air flow resistance, and one or more constrictions to provide the static air flow resistance.

The flow governor can be adapted to change its geometry, and thereby its resistance to air flow, as a function of pressure drop between its inlet and its outlet. The flow governors of the present disclosure therefore provide a means of governing the air flow rate (i.e., volumetric flow rate) through a medicinal inhaler to reduce inter-patient and intra-patient inhalation variability and provide a more reproducible level of drug deposition in the lung. Such flow governors can provide a variable (dynamic) resistance to air flow in an air flow path of a flow governor assembly and/or medicinal inhaler.

Use of an inhaler incorporating one or more flow governors of the present disclosure could provide significant benefits to a sufferer of respiratory or other inhalation-treated disease. Apart from consistency of use and results, flow governors of the present disclosure can avoid the need for bulky spacer devices that are intended to reduce the need for such coordination. When used in conjunction with data recording of flow rates and other inhaler-use events and data, it can also improve physician monitoring of chronically ill patients. When two or more flow governors of the present disclosure are employed in a flow governor assembly and/or a medicinal inhaler, the flow governors can be arranged in parallel or in series.

Flow governors of the present disclosure can include (i) a tubular element that defines at least a portion of an air flow path therewithin, the tubular element comprising one or more flexible walls configured to flex (or collapse) inwardly in response to an air flow in the air flow path, and (ii) an internal support structure located within the tubular element and configured (e.g., shaped, dimensioned, positioned and having desired material properties) to preserve at least a predetermined cross-sectional area of the air flow path within the tubular element when the one or more flexible walls of the tubular element are flexed (or collapsed) inwardly. As a result, part of the air flow path cross-sectional area remains open even when the tubular element has collapsed, in order to allow the continued inhalation of air and emitted medicament. A "predetermined cross-sectional area of the air flow path within the tubular element" can include a portion of the air flow path that passes through the internal support structure, e.g., when the internal support structure includes one or more hollow portions or components, as well as a cross-sectional area of space between the tubular element and the internal support structure. The material makeup of the tubular element flexible walls can also be chosen to achieve the desired cross-sectional area between the tubular element and the internal support structure.

In some embodiments, calculation of the predetermined cross sectional area can be based on the flow resistance required to meet the governing requirements, for example, rearranging the following equation to find 'A':

$$R = \mathrm{sqrt}[0.5 * \rho * (f * 1/d + k)]/A$$

where:
A=cross-sectional area (e.g., $m^2$)
$\rho$=air density (e.g., $kg/m^3$)
f=friction coefficient (dimensionless)
l=length of wall in in the flow direction (e.g., m)
d=tube diameter (e.g., m)
k=singular losses coefficient (dimensionless)
R=flow resistance (e.g., $Pa^{0.5}$*min./L)

Ensuring that the predetermined cross sectional area is maintained can be achieved through use of the internal support structure which physically inhibits the tubular element from collapsing to a point where the cross sectional area is less than the predetermined cross sectional area, and may also include a suitable selection of the material makeup of the flexible walls of the tubular element.

At low inhalation flow rates, the patient experiences a low or moderate static resistance to air flow, but when the inhalation flow rate through the flow governor exceeds a certain flow rate, the tubular element partially collapses and thus imposes an additional resistance to air flow: the inhaler changes from being a low or medium resistance inhaler to a high resistance inhaler. That is, the flow governor provides variable resistance to the assembly comprising the flow governor and/or the inhaler comprising the flow governor (or flow governor assembly).

The present inventors discovered that it can be desirable to have a combination of a static medium resistance and a large variable resistance to make it easier for the patient to inhale with a specific (e.g., target) flow rate. There can be several contributors to the static resistance of a flow governor assembly (or inhaler), such as inlets, outlets, one or more constrictions, the flow governor, other geometrical features of the air flow path, or combinations thereof. As described in greater detail below with respect to FIGS. 20-23, such a constriction can include a venturi section, a narrow passageway, a tortuous path, or a combination thereof. The constriction can be used to add a desired amount of static resistance to the assembly (or inhaler), and can be separate and independent from the flow governor. For example, the constriction can be positioned (i) at a location in the housing upstream of the flow governor, and/or (ii) at a location in the housing downstream of the flow governor, such that the constriction is outside of and separate from the flow governor, i.e., to provide a known static resistance in addition to the flow governor.

The present inventors have recognized that a critical consideration is the balance of the static and variable resistances of a flow governor assembly (or inhaler) comprising a flow governor of the present disclosure, so that the flow governor assembly (or an inhaler comprising the flow governor assembly or the flow governor) can be used by a large proportion of weaker (e.g., COPD) patients with a minimum of inter-patient and intra-patient variability in inhalation flow rate. For example, as mentioned in the 'Summary' above, air flow resistance can be calculated according to the following equation:

$$R = PD^{0.5}/FR$$

where:
R=air flow resistance (e.g., $Pa^{0.5}*(min./L)$)
PD=pressure drop (e.g., Pa)
FR=volumetric air flow rate (e.g., L/min.)

Particularly, the present inventors discovered that at low pressure drops (e.g., 0.5 kPa), a flow governor assembly (or inhaler) having a properly balanced static and dynamic air flow resistance can exhibit a first overall air flow resistance $R_1$, based on the static resistance of the assembly (or inhaler) comprising the flow governor. At higher pressure drops (e.g., 4 kPa), the flow governor assembly (or inhaler) can exhibit a second air flow resistance $R_2$, predominantly based on the relatively large dynamic resistance provided by the flow governor. As a result, the balance of static and dynamic resistances can exhibit appropriate overall air flow resistances at both low pressure drops and high pressure drops to achieve a target governing flow rate over a range of pressure drops.

In some embodiments, the ratio of $R_2/R_1$ (e.g., at a given volumetric flow rate, or to achieve a target governing volumetric flow rate) of a flow governor assembly (or inhaler) comprising the flow governor (and optionally, further comprising a constriction to introduce a desired level of static resistance) can be at least 1.2; in some embodiments, at least 1.3; in some embodiments, at least 1.5; and in some embodiments, at least 2. In some embodiments, the ratio of $R_2/R_1$ (e.g., at a given volumetric flow rate, or to achieve a target governing volumetric flow rate) can be no greater than 3; in some embodiments, no greater than 2.9; in some embodiments, no greater than 2.8; in some embodiments, no greater than 2.7; in some embodiments, no greater than 2.5; and in some embodiments, no greater than 2.

In some embodiments, a flow governor assembly (or inhaler) comprising the flow governor can provide an overall resistance (e.g., $R_1$) to air flow of at least 0.4 $Pa^{0.5}*min./L$ at a pressure drop (i.e., between an air inlet and an air outlet of the air flow path of the assembly (or inhaler)) of 0.5 kPa. In some embodiments, the overall resistance to air flow can be at least 0.5 $Pa^{0.5}*min./L$ at 0.5 kPa; and in some embodiments, at least 0.6 $Pa^{0.5}*min./L$ at 0.5 kPa. In some embodiments, the overall resistance can be no greater than 1.2 $Pa^{0.5}*min./L$ at 0.5 kPa; in some embodiments, no greater than 1.1 $Pa^{0.5}*min./L$ at 0.5 kPa; in some embodiments, no greater than 1.0 $Pa^{0.5}*min./L$ at 0.5 kPa; in some embodiments, no greater than 0.8 $Pa^{0.5}*min./L$ at 0.5 kPa; and in some embodiments, no greater than 0.7 $Pa^{0.5}*min./L$ at 0.5 kPa.

In some embodiments, the overall resistance (e.g., $R_2$) can be at least 1 $Pa^{0.5}*min./L$ at 4 kPa; in some embodiments, at least 1.1 $Pa^{0.5}*min./L$ at 4 kPa; in some embodiments, at least 1.2 $Pa^{0.5}*min./L$ at 4 kPa; and in some embodiments, at least 1.5 $Pa^{0.5}*min./L$ at 4 kPa. In some embodiments, the overall resistance can be no greater than 3.2 $Pa^{0.5}*min./L$ at 4 kPa; in some embodiments, no greater than 3 $Pa^{0.5}*min./L$ at 4 kPa; in some embodiments, no greater than 2.5 $Pa^{0.5}*min./L$ at 4 kPa; in some embodiments, no greater than 2.2 $Pa^{0.5}*min./L$ at 4 kPa; in some embodiments, no greater than 2.0 $Pa^{0.5}*min./L$ at 4 kPa; and in some embodiments, no greater than 1.8 $Pa^{0.5}*min./L$ at 4 kPa.

In some embodiments, the overall resistance to air flow at low pressure drops (e.g., 0.5 kPa), $R_1$, can range from about 1.1 to about 0.4 $Pa^{0.5}*min./L$ (e.g., to achieve a governing flow rate ranging from about 20 L/min. to about 60 L/min.); and in some embodiments, can range from about 0.8 to about 0.6 $Pa^{0.5}*min./L$; and in some embodiments, can range from about 0.7 to about 0.5 $Pa^{0.5}*min./L$.

In some embodiments, the overall resistance to air flow at high pressure drops (e.g., 4 kPa), $R_2$, can range from about 3.2 to about 1.0 $Pa^{0.5}*min./L$ (e.g., to achieve a governing flow rate ranging from about 20 L/min. to about 60 L/min.); and in some embodiments, can range from about 2.5 to about 1.5 $Pa^{0.5}*min./L$; and in some embodiments, can range from about 2.3 to about 1.8 $Pa^{0.5}*min./L$.

The flow governors of the present disclosure are suitable for use in multiple forms of inhalers for the delivery of doses of medicament in the form of aerosols to the respiratory tract, including oral pulmonary inhalers and nasal inhalers. Flow governors of the present disclosure are suitable for use in a variety of inhalers, including but not limited to, one or more of a pressurized metered dose inhaler (pMDI) (e.g., a press-and-breathe pMDI, a mechanical (i.e., mechanically triggered) breath-actuated pMDI, an electronic (i.e., an electronically triggered) breath-actuated pMDI, or a combination thereof); a dry powder inhaler (e.g., a single dose (e.g., capsule) DPI, a multi-dose (e.g., tape based, or reservoir based) DPI, or a combination thereof); a nebulizer (e.g., a pocket nebulizer); or a combination thereof.

GB Patent No. 2266466 discloses an exemplary electronically triggered breath-actuated pMDI that could be modified to incorporate a flow governor of the present disclosure. PCT Publication No. WO 2015/34709 discloses an exemplary DPI that could be modified to incorporate a flow governor of the present disclosure. PCT Publication No. WO 92/12799 discloses an exemplary pocket nebulizer that could be modified to incorporate a flow governor of the present disclosure. A flow governor of the present disclosure can be used in any of the inhalers disclosed in GB Patent No. 2266466, PCT Publication No. WO 2015/34709, PCT Publication No. WO 92/12799 (each of which is incorporated herein by reference in its entirety), or a combination thereof.

For example, some embodiments of the present disclosure provide a medicinal inhaler comprising a flow governor and a breath actuation mechanism. In some embodiments, the breath actuation mechanism can be configured to trigger to release a dose of medicament at an inspiratory flow rate less than a governing flow rate of the flow governor.

Generally, it is important that the triggering flow rate is not set too low, to avoid the risk that the breath-actuated inhaler might operate accidentally or that it will deliver the medicament at too low an inhalation rate for adequate therapeutic effect. It is also important that the triggering flow rate is not set so high that a patient (e.g. a weak COPD patient) cannot achieve the triggering flow rate.

The triggering flow rate of the breath-actuation system needs to be below the governing air flow rate, in order that the latter does not prevent the triggering flow rate from being achieved. For example, in some embodiments, the target triggering flow rate of an inhaler can be 15 liters/minute (L/min.) and the target governing flow rate can be 30 L/min. In reality, a "target governing flow rate" may actually include a range of flow rates, as described in the Examples section with reference to FIGS. 24 and 25, such that the target governing flow rate may actually be a target range of flow rates. Manufacturing tolerances can be maintained such that individual inhalers all have an actual triggering flow rate of significantly less than their governing flow rate. Environmental factors such as temperature and atmospheric pressure will also broaden the range of values actually obtained. For example, actual triggering flow rates might vary between 10 L/min. and 20 L/min., and actual governing flow rates might vary between 25 L/min. and 35 L/min.

Some embodiments of the present disclosure provide a medicinal inhaler comprising a flow governor and an inspiratory air flow detection (or "inspiratory flow rate detection system," or "air flow detection system," or "flow rate detection system," or derivations thereof) and/or measurement system. In some embodiments, such a detection system can include at least one pressure sensor located in the inhaler and configured to allow the inspiratory air flow rate to be sensed. For example, at least one pressure sensor can be located upstream of the flow governor in an air flow path of the medicinal inhaler. In some embodiments, such a detection system can include (i) a pressure sensor located in fluid communication with the air flow path, upstream of the flow governor, and (ii) a venturi constriction in the air flow path located adjacent where the pressure sensor is in fluid communication with the air flow path. Such a venturi constriction can speed up the local air velocity to enhance the sensitivity of the pressure sensor, allowing for less sensitive, and less costly, sensors to be employed. Such a detection system can further include a second pressure sensor located in fluid communication with the air flow path, downstream of the flow governor, such that air flow direction can be determined, i.e., in order to distinguish between inhalation and exhalation.

Some embodiments of the present disclosure provide a medicinal inhaler comprising a flow governor, a breath actuation mechanism, and an inspiratory air flow detection system.

In some embodiments of the present disclosure, the breath-actuation system can be an electronically triggered breath-actuation system. For example, the one or more pressure sensors can provide an electrical signal which is used to trigger dose release according to a defined algorithm. The dose release system may be a mechanical system, triggered by the electronic system's algorithm. Optionally, the electronic system may be housed in a reusable module, in order to reduce the overall cost of a prolonged period of treatment.

Additional details of flow governors are described in PCT Publication No. WO2017/112748, which is incorporated herein by reference in its entirety.

Dose release firing systems that can be employed in combination with flow governors of the present disclosure are described in PCT Publication Nos. WO2017/112476 and WO2017/112400, each of which is incorporated herein by reference in its entirety. In addition, auto-reset dose release firing systems that can be employed in combination with flow governors of the present disclosure are described in PCT Publication No. WO2017/112451, which is incorporated herein by reference in its entirety.

Some firing systems (e.g., which can be used in combination with flow governors of the present disclosure) can produce a small time delay between the start of inhalation and the time when the medication is released. Desirably, medication release occurs within 0.5 sec of the start of inhalation. A typical COPD patient has a tidal lung capacity of about 1.5 L. If the inhalation flow rate is limited by the flow governor to about 30 L/min., then the time of inhalation could be expected to extend to about 3-4 seconds. In reality, COPD patients may not be able to inhale for this long, due to their poor lung function, but it is anticipated that there will be sufficient time for drug to be transferred to the lung.

Some embodiments of the present disclosure provide a method of treatment of a pulmonary condition in a human patient, the method comprising: (i) providing a medicinal inhaler incorporating a flow governor comprising the tubular element and internal support structure described above; (ii) inserting a patient port of the medicinal inhaler into a body cavity (e.g., a mouth or nose); and (iii) actuating the medicinal inhaler while inhaling.

In some embodiments, the present disclosure can provide a method of using a medicinal inhaler, or of treating a pulmonary condition, which can include providing a flow governor of the present disclosure in an air flow path of the medicinal inhaler, and varying an air flow resistance of the inhaler in response to air flow in the air flow path of the flow governor. The method can further include inserting a patient port into a body cavity; and inhaling through the patient port to cause air flow in the air flow path of the flow governor. Varying the air flow resistance of the inhaler can include flexing one or more tubular walls of a tubular element of the flow governor inwardly toward an internal support structure located within the tubular element, the internal support structure configured to preserve at least a predetermined cross-sectional area of the air flow path within the tubular element when the one or more tubular walls flexes inwardly.

Definitions

The terms "a", "an", and "the" are used interchangeably with "at least one" to mean one or more of the elements being described.

The term "and/or" means either or both. For example "A and/or B" means only A, only B, or both A and B.

The terms "including," "comprising," or "having," and variations thereof, are meant to encompass the items listed thereafter and equivalents thereof as well as additional items.

Unless specified or limited otherwise, the terms "connected" and "coupled" and variations thereof are used broadly and encompass both direct and indirect connections and couplings. Further, "connected" and "coupled" are not restricted to physical or mechanical connections or couplings.

The term "flexible" is used to refer to a material and/or structure that collapses or significantly deforms in response to an air pressure differential existing across the material and/or structure in its typical mode of operation. The term 'rigid' is used to refer to a material and/or structure that does not collapse or significantly deform under the forces it experiences in its typical mode of operation. For example, the tubular element of flow governors of the present disclosure is generally flexible and deformable in its normal operation, whereas the internal support structure of flow governors of the present disclosure is generally rigid or non-deformable in its normal operation.

The term "tubular" is used to refer to a hollow structure having one or more walls that define an open passageway therein. In some embodiments, the term "tubular" can more specifically refer to elongated hollow structures. Tubular elements of flow governors of the present disclosure or tubular air flow paths of the present disclosure can have any cross-sectional shape desired (i.e., transverse cross-sectional shape—taken substantially orthogonally with respect to a longitudinal axis of the tubular structure), including, but not limited to, one or more of circular, elliptical or oblong (i.e., having a longer major axis and a shorter minor axis), triangular, rectangular, square, trapezoidal, polygonal, star-shaped, D-shaped, other suitable cross-sectional shapes, or a combination thereof. In some embodiments, tubular structures of the present disclosure can have a circular cross-sectional shape.

The present disclosure will be described with respect to particular embodiments and with reference to certain drawings but the invention is not limited thereto. The drawings described are only schematic and are non-limiting. In the drawings, the size of some of the elements may for illustrative purposes be exaggerated and not drawn to scale. Identical, similar or equivalent features in different embodiments have been denoted by similar numerals but with the addition to them of 100, 200, 300, etc.

Before describing the embodiments in accordance with the present invention, a typical embodiment of a conventional pMDI device will be described with reference to FIG. 1.

FIG. 1 illustrates a conventional pressurized metered dose inhaler (pMDI) 50 comprising a canister 51 containing a medicament formulation 52, the canister comprising a can 53 sealed with a metering valve 54. The canister 51 sits within a housing (or "actuator") 55 comprising a tubular sleeve portion 56 having an open end 47 dimensioned to receive the canister 51 and from which its base 49 can protrude, and a portion in the form of a patient port 57 (e.g., in the form of a mouthpiece) that defines an inspiration orifice (or an air outlet) 45. Such a patient port of an inhaler is sometimes referred to herein as a "mouthpiece" for simplicity. However, it should be understood that such mouthpieces can instead be configured to be nosepieces of nasal inhalers and that the present disclosure can equally apply to nasal inhalers even where not specifically mentioned herein. The open end 47 of the housing 55 can define an aspiration orifice, or an air inlet, and the air outlet 45 can define an inhalation orifice, or an air outlet.

A stem portion 58 protrudes from the metering valve 54 and is located and retained by friction in a stem socket 59 formed as an integral part of the housing 55. A spray orifice 60 is formed in the stem socket 59, and provides a passage for fluid communication between the valve stem portion 58 and the inspiration orifice 45. In use, a patient places the patient port (e.g., mouthpiece) 57 into a body cavity (e.g., mouth) and then inhales through it while at the same time pressing downwards on the protruding base 49 of the canister 51. The pressing force serves to move the canister 51 downwards relative to the valve's stem portion 58. That relative movement serves to isolate a metered dose of medicament formulation from the bulk formulation in the canister 51 and then to discharge it via a hollow bore 48 formed in the stem portion 58. The discharged dose then passes along the fluid passageway through the stem socket 59 and the spray orifice 60 and emerges in the form of a fine respirable spray 61 that passes through the patient port 57 into the patient's body cavity (e.g., oral cavity and/or nasal cavity) and thence into their respiratory passages, thereby treating their disease.

Important aspects of such a conventional pMDI device 50 that have the potential to limit its efficacy are, in particular, its fixed low resistance to air flow and its need for good patient coordination between the timing of the start of inhalation and the moment at which the canister 51 is pressed downwards. The latter is a challenge for a high proportion of patients, leading to poor and often highly varying efficacy of medicament administration.

The low resistance air flow path is best described with reference to FIG. 1. As the patient inhales on the patient port 57, i.e. as they reduce the air pressure in their own respiratory passages and oral cavity and in the patient port 57 via outward movement of their chest wall and downwards movement of their diaphragm, an air flow is set up through the pMDI device 50. Air from the atmosphere external to the inhaler, i.e., ambience, is drawn into the inhaler via an air flow path 46 of the pMDI device 50, e.g., beginning with the annular gap between the can 53 and the open tubular sleeve portion 56 of the housing 55, passing down the sleeve portion 56 along the length of the can 53, and turning the corner into the wide passageway inside the mouthpiece 57. The mouthpiece passageway clearly needs to be open and wide to allow the medicament spray 61 to emerge. The annular gap also has a large cross-sectional area that is approximately a product of the canister diameter (typically 22-23 mm) and the clearance required between the canister 51 and the housing sleeve portion 56 to ensure that the canister 51 does not scrape or jam within the housing 55. Typically this clearance is 2 mm or more, giving an approximate air flow path cross-sectional area of in excess of 40 mm$^2$. At the typical patient inspiratory pressure drops of 0.5 to 8 kPa, that cross-section presents very little effective resistance to inspiratory air flow. It is thus easy for many patients to draw an excessive and uncontrolled flow rate of air through the inhaler, leading to poorly controlled and inconsistent medicament delivery to their lungs.

Figure 2:
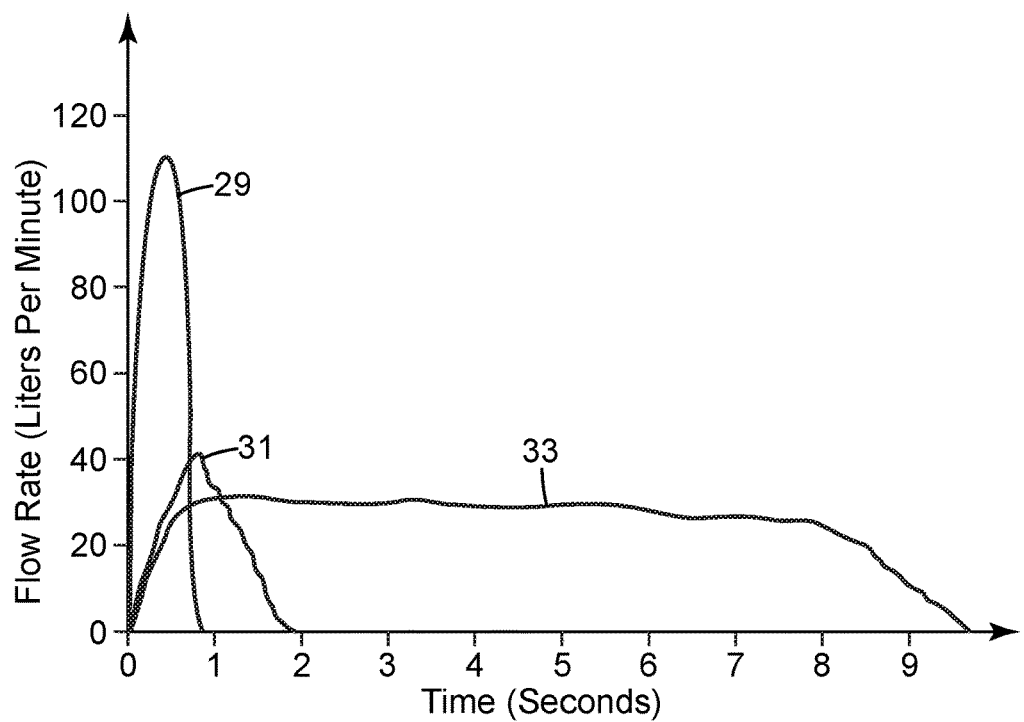
FIG. 2 is a graph schematically illustrating flow rate (L/min.) versus time (seconds) of inhalation flow profiles of COPD patients using conventional medicinal inhalers and using medicinal inhalers comprising a flow governor of the present disclosure.
Figure 3:
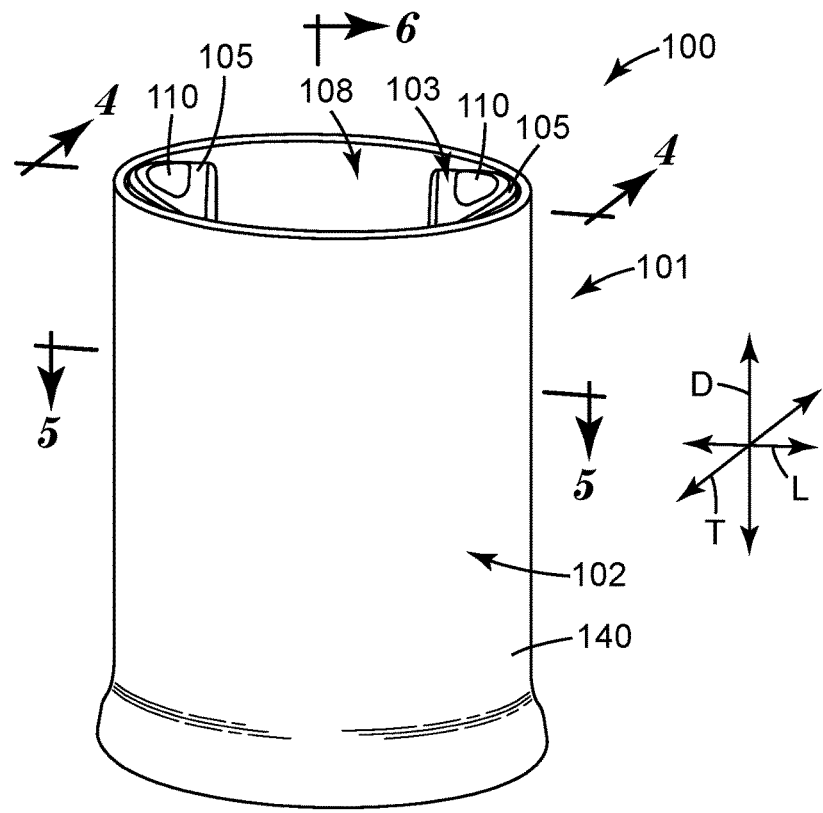
FIG. 3 is an isometric view of a flow governor according to one embodiment of the present disclosure, shown at rest.

FIG. 2 shows, schematically, some fairly typical chronic obstructive pulmonary disease (COPD) patient inspiratory flow rate (L/min.) versus time (seconds) profiles. In the absence of significant inhalation device resistance to air flow, some profiles 29 are characterised by a short, relatively rapid intake of breath. Other patients, e.g. with weaker lungs, are unable to either sustain long inhalations or to achieve adequate flow rates. Their profiles 31 are short and weak. Using an inhaler that comprises a flow governor of the present disclosure, however, can provide patient inspiratory profiles that are more like that denoted as 33: a longer, sustained, steady inspiratory flow rate (e.g., of around 30 L/min.) can be obtained.

COPD patients have a wide range of inhalation breathing capability and this can be represented as a distribution between 0.5 and 4 kPa pressure drop. In some embodiments, the static resistance of an inhaler of the present disclosure prior to any governing of flow by the flow governor of the present disclosure (i.e., prior to any collapse of the tubular element) can be approximately 0.8 $Pa^{0.5}$ min./L. This can be considered to be a medium resistance. In some embodiments of the present disclosure, the target governing flow rate can be 30 L/min. In some embodiments, the target breath-actuation triggering flow rate can be 15 L/min. With such a system, there is very low probability of a COPD patient not being able to reach the triggering flow rate, either through lack of inhalation effort or because any individual flow governor limits the air flow rate to less than its breath-actuation triggering flow rate. Such an inhalation device is therefore suitable for a very high proportion of COPD patients. That is, at low flow rates, the inhaler will operate like a medium resistance device, and every patient will be able to inhale up to 20 L/min. quite easily. At a somewhat greater flow rate, the flow governor's tubular element will collapse onto the internal support structure, and the inhaler will become a high resistance device. The patient will then not be able to inhale at a higher flow rate. In general, patients are likely to learn to automatically compensate their inhalation effort and will continue to inhale at a flow rate that is comfortable to them. For some patients, that will involve a pressure drop of only 0.5 kPa, but for others it will be 4 kPa or above depending upon their lung strength and capacity and upon the training the patient has previously had.

If a higher flow governor flow rate were selected (e.g., greater than 30 L/min.), then some patients would not be able to achieve the air flow rate required for the inhaler to be governed, and the variability in patient inhalation would not be minimized. If, alternatively, the inhaler were to have a higher resistance, then again some patients would not be able to achieve the governed flowrate and the variability in patient inhalation flowrate would not be minimized. With the parameters described above, however, an inhaler incorporating a flow governor of the present disclosure has the potential to:

Improve coordination of drug release with the start of inspiratory flow;

Maintain the inspiratory air flow rate to within a range of approximately 25 to 35 L/min.; and Reduce variability both in dose consistency and the location of drug deposition in the lung.

For a nominal target governing flow rate of 30 L/min., there will be a range of actual values due to manufacturing tolerances and environmental factors such as temperature and atmospheric pressure. In an embodiment where the inhaler's total static resistance is 0.83 $Pa^{0.5}(minl^{-1})$, and the flow governor has a nominal governing flow of 30 L/min., any patient inhaling at a pressure drop between 0.5 kPa and 4 kPa would be expected to generate an air flow of between about 25 and 35 L/min.

In some embodiments of the present disclosure, the governing flow rate can be nominally 40 L/min. In this case, patients who can only produce a low inhalation pressure drop (e.g. about 0.5 kPa) and who typically inhale at less than 40 L/min. will not benefit from the flow governor, and their inhalation will be equivalent to inhaling through a medium resistance inhaler. Other patients who naturally inhale more strongly (i.e. at a higher pressure drop) are likely to benefit from the flow governor, and their flow rate will be restricted by the flow governor to the governing flow rate.

In some embodiments of the present disclosure, the governing flow rate can be nominally 50 L/min. In this case, only patients who inhale at a pressure drop of greater than approximately 1.5 kPa will experience flow governing. Because the governing flow rate is higher, there will be a larger spread in the Peak Inhalation Flow rates (PIF) obtained between patients: some will be able to inhale at only around 27 L/min. because this is the fastest that they can inhale through a medium resistance device, whereas others who inhale at 4 kPa could pull as much as 55 L/min. through the system.

Additional illustrations of the effects of flow governors are detailed below in the Examples section.

FIGS. 3-14 illustrate various embodiments of flow governors of the present disclosure. FIGS. 15-19 illustrate various embodiments of medicinal inhalers of the present disclosure that comprise a flow governor of the present disclosure. FIGS. 20-23 illustrate various embodiments of flow governor assemblies of the present disclosure, comprising flow governors that can be employed in medicinal inhalers.

Flow Governors

Figure 5:
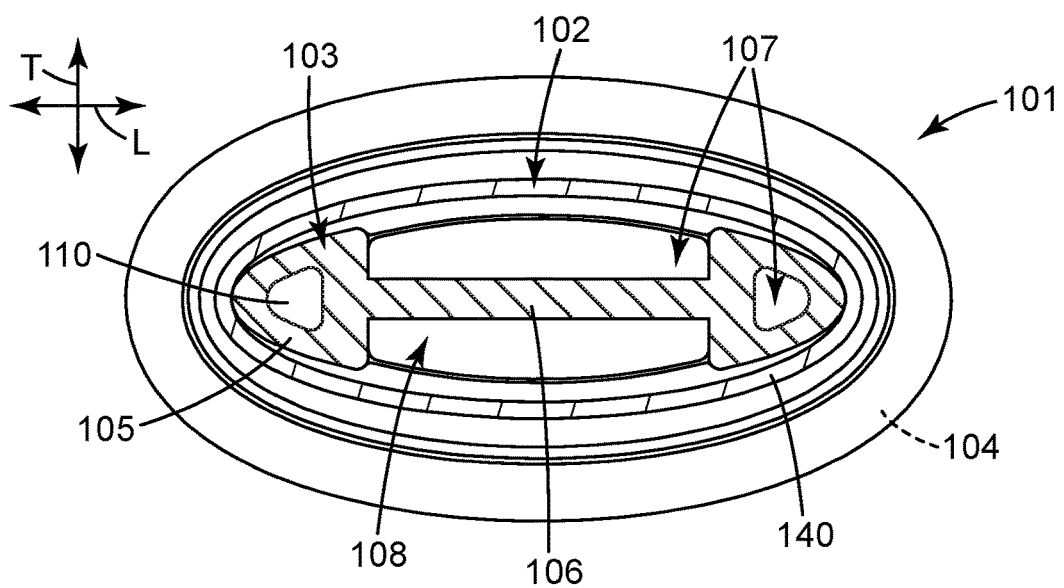
FIG. 5 is a transverse cross-sectional view of the flow governor of FIGS. 3 and 4, taken alone line 5-5 of FIG. 3, shown at rest.
Figure 6:
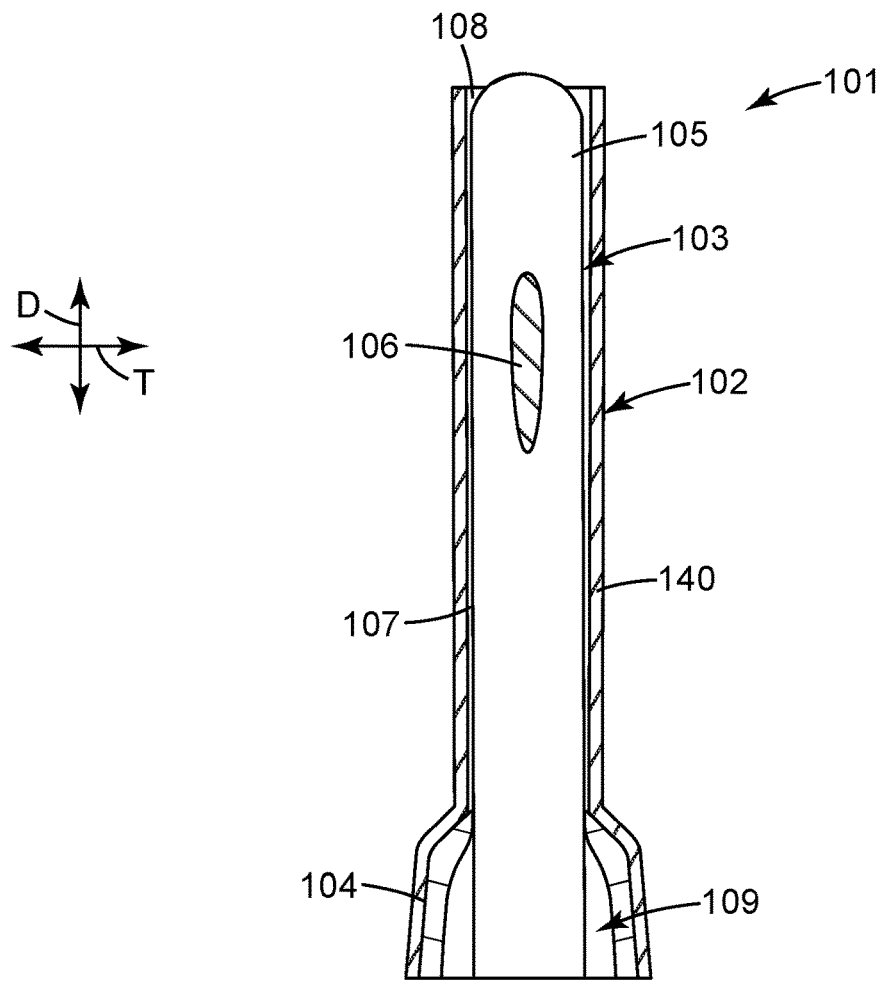
FIG. 6 is a side longitudinal cross-sectional view of the flow governor of FIGS. 3-5, taken along line 6-6 of FIG. 3, shown at rest.
Figure 7:
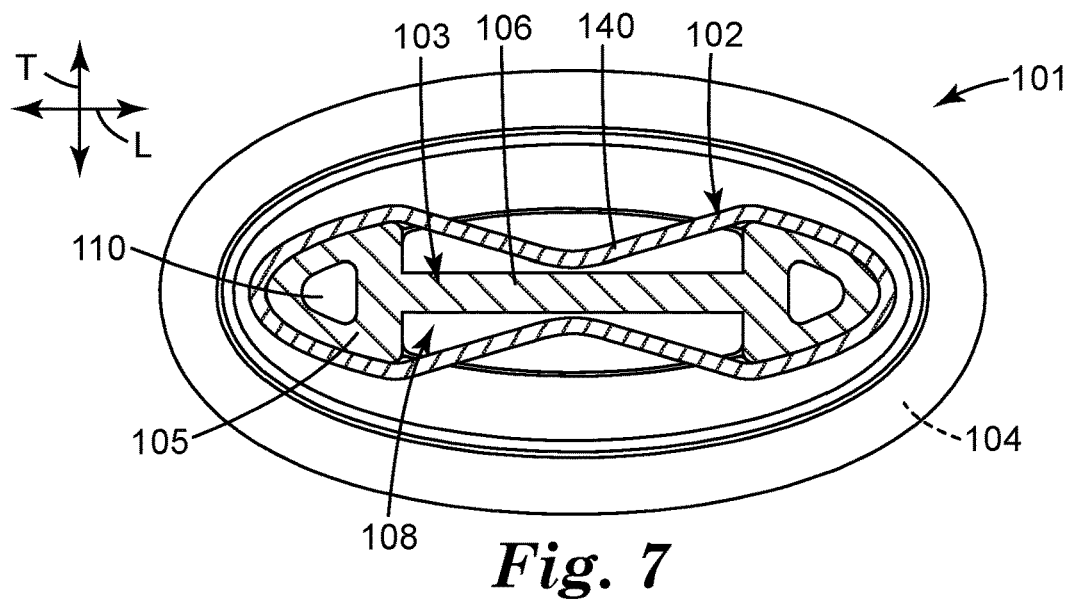
FIG. 7 is a transverse cross-sectional view of the flow governor of FIGS. 3-6, taken alone line 5-5 of FIG. 3, shown in operation.
Figure 8:
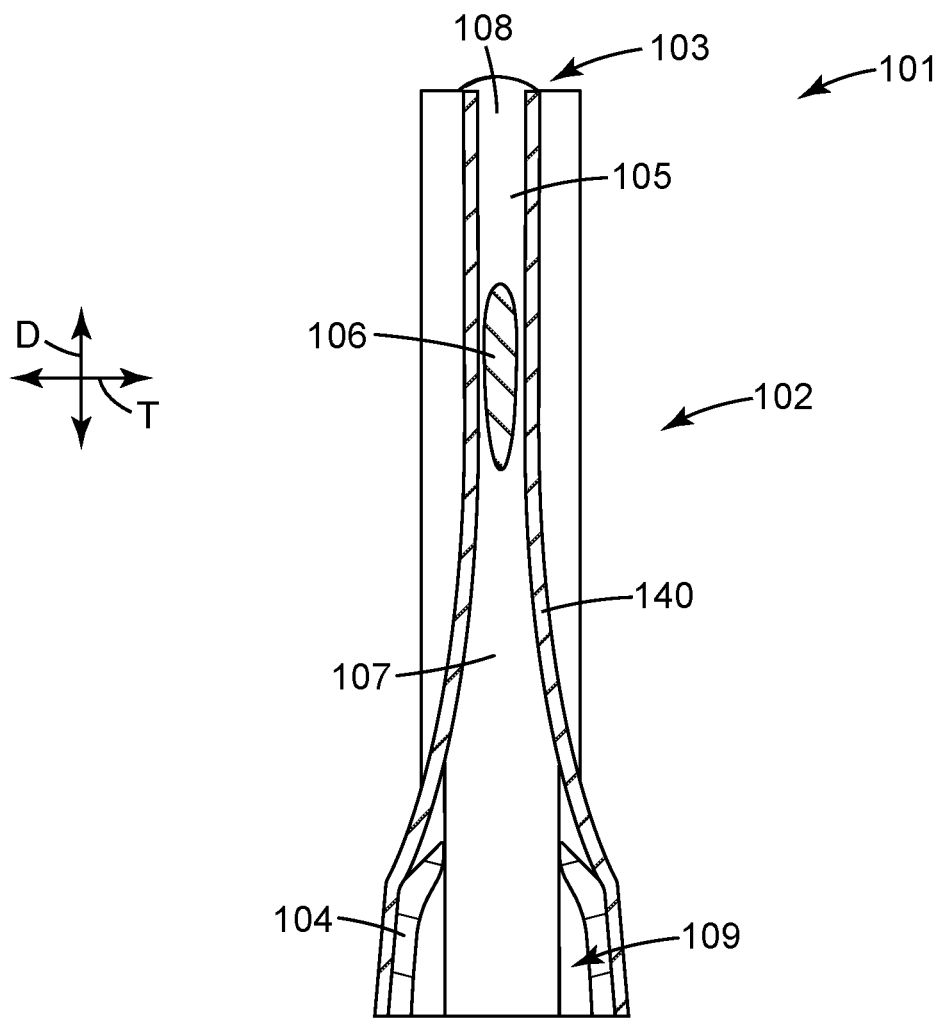
FIG. 8 is a side longitudinal cross-sectional view of the flow governor of FIGS. 3-7, taken along like 6-6 of FIG. 3, shown in operation.

FIGS. 3-8 illustrate a flow governor 101 according to one embodiment of the present disclosure. FIGS. 3-6 show the flow governor 101 at rest, and FIGS. 7-8 show the flow governor 101 in operation.

As shown, the flow governor 101 includes an outer flexible tubular element (or "tube") 102 comprising at least one flexible wall 140, and an internal support structure 103 that is dimensioned to be received within the tubular element 102 (i.e., within the at least one flexible wall 140). In the embodiment of FIGS. 3-8, the internal support structure 103 includes a hollow base 104, two hollow (e.g., tubular) pillars 105 and a cross member (or "crossbeam") 106.

The outer diameter of the hollow base 104 of the illustrated embodiment is greater than an initial inner diameter of the tubular element 102, and assembly of the two components can be achieved by stretching the tubular element 102 over an outer portion (e.g., an outer wall) of the hollow base 104. This positioning results in the originally circular cross-section of the tubular element 102 being deformed into an approximately elliptical (or oblong) cross-sectional (i.e., in transverse cross-section) shape. In some embodiments, such an elliptically-shaped tubular element 102 can have a major axis (externally) of approximately 12 mm and a minor axis (externally) of approximately 4 mm.

Other formation and/or assembly means are alternatively possible, however, as will be apparent to a person of ordinary skill in the art. For example, the tubular element 102 could instead be over-molded onto an outer surface of the hollow base 104 of the internal support structure 103, or it could be stretched and then coupled to the outer surface of the base 104 by a variety of coupling means, including, but not limited to, one or more of adhesives, cohesives, welding (e.g., sonic [e.g., ultrasonic] welding), any thermal bonding or heat sealing technique (e.g., heat and/or pressure applied to one or both of the components to be coupled), other suitable coupling means, or combinations thereof.

In some embodiments, the internal support structure 103 can be coupled to or integrally formed with a portion of a housing that forms an air flow path or an inhaler of the present disclosure. For example, in some embodiments, the internal support structure 103 can be provided by (e.g., integrally formed with) the housing that forms at least a portion of an inhaler housing.

As shown in FIGS. 3-6, the flow governor 101, and the tubular element 102, can be substantially linear. Furthermore, the flow governor 101 can have an air flow path 107 including an air inlet 108 located at a first (longitudinal) end and an air outlet 109 located at a second (longitudinal) end that generally define an air flow direction that is generally oriented along a longitudinal direction D. The tubular element 102 can be elongated in the longitudinal direction D. The at least one flexible wall 140 of the tubular element 102 can be oriented substantially parallel to the longitudinal direction D; the hollow pillars 105 can be oriented substantially parallel to the longitudinal direction D; and the cross member 106 can be oriented at a non-zero angle (e.g., substantially perpendicularly) with respect to the longitudinal direction D, i.e., substantially parallel with respect to a lateral direction L (which can represent a side-to-side direction of the flow governor 101). A third transverse direction T is oriented substantially perpendicularly with respect to the longitudinal direction D and the lateral direction L, and can represent a front-to-back direction of the flow governor 101.

The tubular element 102 (i.e., the at least one flexible wall 140) can be formed of a variety of materials, including, but not limited to, one or more of silicone rubber, other thermoplastic elastomers, or combinations thereof. In addition to its flexibility, the tubular element 102 can be formed of a material that is resilient, in order that it returns to its rest shape and position when air flow through it ceases, i.e., the tubular element 102 can deform elastically and spring back ready for its next cycle of use. The material may be chosen according to specific property needs, e.g. if it is to be over-molded, glued or ultrasonically welded to the hollow base 104 of the internal support structure 103. It will be obvious to one skilled in the art that the chosen tubular element material should have good long term physical and chemical stability.

While the tubular element 102 can suitably have a relaxed transverse cross-sectional shape that is substantially circular (and which can be stretched to an elliptical cross-sectional shape over the base 104 of the internal support structure 103), other cross-sectional shapes are possible, such as those described above in the definition of "tubular." It should also be noted that the base 104 can be elliptical in its transverse cross-sectional shape or can be another shape. In some embodiments, the base 104 is elliptical, the ellipse having the special case shape of a circle. In some embodiments employing a transverse cross-sectional shape of the base 104 that is circular, or is close to circular, can assist in ensuring that the tubular element 102 can be assembled onto it without imposing significant residual torsional strains into it. Furthermore, in some embodiments, the tubular element 102 can be formed of more than one material, or can have different sections (e.g., sequentially along its longitudinal direction) with different wall thicknesses and/or diameters, such that certain sections of the tubular element 102 are more flexible than others and can preferentially collapse.

In some embodiments, the tubular element 102 can be formed of a silicone rubber tube of approximately 0.3 mm wall thickness, 8.0 mm initial inside diameter, 20 mm length and 60 OO Shore hardness.

Figure 4:
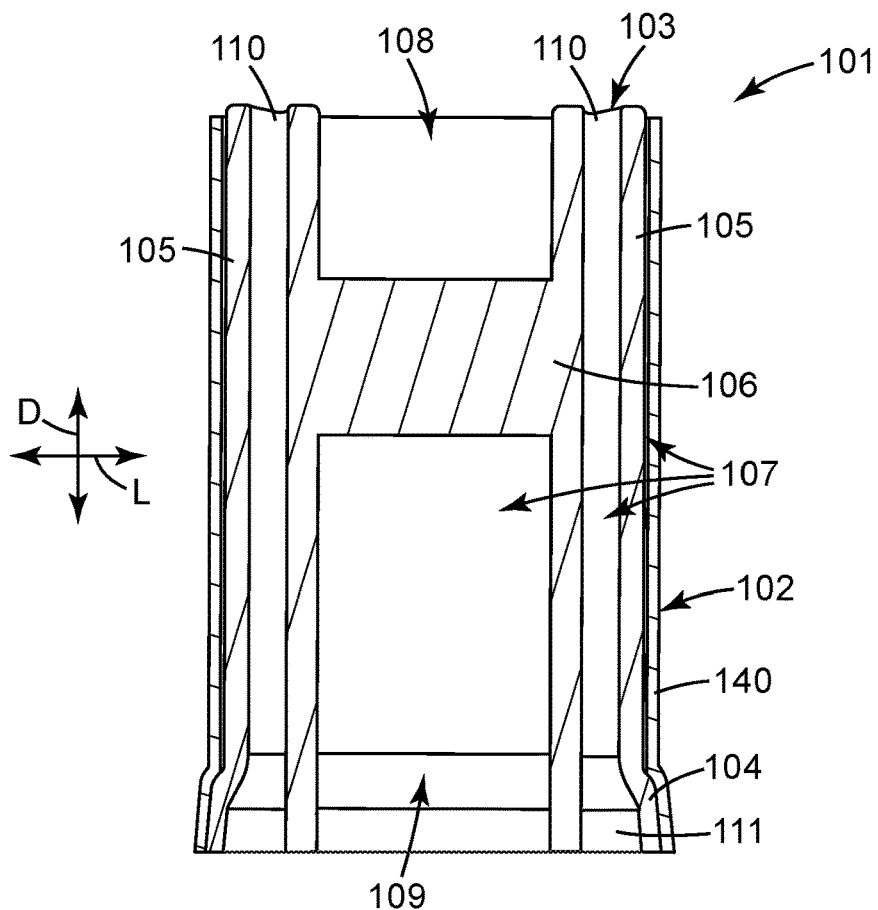
FIG. 4 is a front longitudinal cross-sectional view of the flow governor of FIG. 3, taken along line 4-4 of FIG. 3, shown at rest.

In some embodiments, the internal support structure 103 can have an "H" shaped longitudinal cross-sectional shape (i.e., taken along the longitudinal direction D), as shown in FIG. 4. However, as shown in FIG. 4, in some embodiments, the cross member 106 may not be longitudinally centered with respect to the overall dimension (e.g., height) of the internal support structure 103 in the longitudinal direction D, but rather, the cross member 106 may be located toward the air inlet end (e.g., an upstream end) of the internal support structure 103.

Additionally, or alternatively, in some embodiments, the internal support structure 103 can have a generally "H" shaped (i.e., generally similar to a capital English letter H) transverse cross-sectional shape (i.e., taken substantially orthogonally with respect to the longitudinal direction D, e.g., in the lateral direction L or the transverse direction T), as shown in FIG. 5. Furthermore, in some embodiments, the internal support structure 103 can be formed of an injection molded plastic, such as polypropylene, acetal, ABS (acrylonitrile butadiene styrene), polycarbonate or polyethylene, or can be made from a metal or metal alloy (e.g., machined, stamped/pressed or metal injection molded) or from a ceramic material (e.g. ceramic injection molded). In some embodiments, the internal support structure 103 can be formed as a single integral component, i.e., formed from one part.

As shown in FIG. 5, in some embodiments, the cross member 106 of the internal support structure 103 can be substantially centered with respect to the pillars 105 in the transverse direction T, which gives the generally "H" shaped transverse cross-sectional shape. In addition, by way of example, the illustrated internal support structure 103 of FIGS. 3-8 has lateral symmetry about a central longitudinal axis (i.e., about a central transverse-longitudinal plane), as well as transverse symmetry (e.g., front-to-back) about the central longitudinal axis (i.e., about a central lateral-longitudinal plane). Said another way, the internal support structure 103 is symmetrical about a central longitudinal axis in the lateral direction D and the transverse direction T.

As will be described in greater detail below, only the air outlet end of the tubular element 102 is fixed and supported (i.e., by the base 104 of the internal support structure 103), whereas the air inlet end of the tubular element 102 is freestanding and able to collapse onto the internal support structure 103.

The assembly of the tubular element 102 and the internal support structure 103 forms the air flow path 107, including the air inlet 108 and the air outlet 109. FIG. 5 shows a transverse cross-section of the flow governor 101, which illustrates that the tubular element 102 has an approximately elliptical cross-section once stretched onto the base 104 of the internal support structure 103, and also shows two lumens 110, located within the two hollow pillars 105, which act as residual air flow channels, i.e., function as a portion of the air flow path 107 through the flow governor 101. By way of example only, the lumens 110 are shown as having an approximately triangular shape in the transverse cross-section. In some embodiments, each of the two lumens 110 can have an open cross-sectional area of approximately 1 mm$^2$.

FIG. 6 shows a side longitudinal cross-section of the flow governor 101, which illustrates that the tubular element 102 runs substantially parallel to the hollow pillars 105, but is not in contact with them. At the air inlet 108, the hollow pillars 105 can protrude from the tubular element 102. With reference to FIG. 4, it may be noted that air flow entering the pillar lumens 110 will exit at a bypass outlet 111 of each pillar 105, prior to passing through the hollow base 104.

One primary function of the flow governors of the present disclosure is to govern air flow when the patient inhales through a medicinal inhaler, limiting the patient's inspiratory flow rate to a narrow and controlled range in order to avoid excessively fast inhalation and consequently excessive mouth and throat drug deposition. The flow governors of present disclosure are thus able to aid in the attainment of increased deep lung drug penetration and deposition.

Use of such a flow governor allows patients with poor lung function (e.g. particularly poorly COPD patients) to experience a relatively low inhaler air flow resistance (allowing them to inhale sufficient air in a reasonable degree of comfort) while giving patients with stronger lungs a transiently higher air flow resistance to inhale against (thereby allowing them to inhale for longer and more deeply, while at the same time limiting their inhalation air flow rate to a level very similar to that of weaker patients). In other words, the inspiratory air flow rate can be kept much more consistent between patients and between inhalations. Medication delivery is thus much more predictable, allowing physicians to prescribe treatment regimes with an improved level of confidence.

While FIGS. 3-6 illustrate the flow governor 101 at rest (i.e., with the tubular element 102 in an uncollapsed state); FIGS. 7 and 8 show the flow governor 101 in an operative state (i.e. with the patient's inspiratory air flow substantially passing through it and with the tubular element 102 in a collapsed state). When air is sucked towards the air outlet 109, it flows via the air inlet 108 into the air flow path 107, around the pillars 105 and cross member 106 (i.e., through any gap still present between the pillars 105 and the tubular element 102 and between the cross member 106 and the tubular element 102), and through the pillar lumens 110. The speed of the passing air flow through the air flow path 107 creates a reduction in air pressure in the air flow path 107 (i.e., according to the Bernoulli Effect). In the embodiment illustrated in FIGS. 3-8, the reduced pressure in the air flow path 107 causes a reduction in the diameter along the minor axis of the elliptical cross-sectioned tubular element 102 (i.e., in the transverse direction T) resulting in inward bending, as shown in FIGS. 7 and 8. Because the tubular element 102 is supported at one end (i.e., its outlet end, toward the air outlet 109) by the hollow base 104, the inward bending occurs predominantly at the end of the tubular element 102 that is towards the air inlet 108, the inward bending restricting the cross-sectional area of the air flow path 107.

To an extent, the greater the reduction in pressure in the air flow path 107, the greater the inward bending of the tubular element 102. The resultant reduction in the cross-sectional area of the air flow path 107 leads to an increased resistance to air flow rate. However, because the air flow path 107 of the flow governor 101 is only one part of the total overall resistance to air flow of the medicinal inhaler in which the flow governor 101 is employed (e.g. it might be around 50% or less of the total inhaler air flow resistance if the inhaler has a moderate static resistance to air flow), then the mass flow rate of air through the flow governor 101 does not fall in proportion to its reduced residual cross-sectional area. This means that the velocity of air through the residual air flow path 107 within the collapsed tubular element 102 rises as the tubular element 102 collapses, further increasing the Bernoulli forces upon it. This effect tends to lead to substantial bistability in the operation of the flow governor 101. That is, the initiation of collapse leads to "positive feedback" which reinforces the inwards collapse-driving Bernoulli forces until they are eventually balanced by the resistive stiffness forces of the material of the tubular element 102. In other words, in some embodiments, the flow governor 101 can be substantially bistable, where it tends to be in one of two states at any time: either it is in a substantially 'open' or 'uncollapsed' state, or it is in a substantially 'collapsed' state.

Complete collapse of the elliptical cross-section tubular element 102 is prevented by the hollow pillars 105. These pillars 105, together with the cross member 106, provide structural support that prevents significant reduction in the diameter along the major axis of the elliptical cross-section tubular element 102 (i.e., in the lateral direction L). The air flow bypasses provided by the lumens 110 allow a base level of residual air flow to continue to flow. In addition, the finite stiffness of the tubular element 102 means that small additional gaps are left around the corners of the internal support structure 103 where the tubular element 102 cannot bend sufficiently to close off all the small residual air passageways or gaps between the internal support structure 103 and the tubular element 102 (see, e.g., FIG. 7). Thus, at least a minimum, or residual, air flow can always continue to flow. That is, the reduced pressure can never reach a value sufficient for the tubular element 102 to collapse completely and to seal off all air flow through the flow governor 101.

The point at which the tubular element 102 collapses and the flow rate at which the flow governor governs are dependent on the geometry of the internal support structure 103 (and particularly, on the cross-sectional area of the pillar lumens 110), and the properties of the tubular element 102, in particular its wall thickness, air inlet cross sectional area, width, length and Shore hardness. For the tubular element 102, material that has a low adhesive characteristic can also be preferable, to ensure a smooth transition from the collapsed to the open state by prevention of adhesion to a housing wall of an inhaler in which the flow governor 101 is positioned and/or to the internal support structure 103.

As described in greater detail in the Examples section, mathematical modeling of flow governors of the type shown in FIGS. 3-8 has demonstrated that the flow governors of one embodiment of the present invention are capable of governing at an air flow of 30 L/min. with a repeatability and consistency of ±5 L/min. over a wide range of patient pressure drops. Almost all patients, even those with very weak lungs, should be capable of achieving such air flow rates, yet because of the operation of the flow governor, no patients are likely to be able to exceed such air flow rates, even with very excessive effort.

Other arrangements of the embodiment described, such as the shape, size, number and location of elements belonging to the internal support structure, will be apparent to one skilled in the art.

Other designs or configurations of the internal support structure may be used instead of the hollow pillar and cross member arrangement of FIGS. 3-8. For example, FIGS. 9-14 illustrate various flow governors of the present disclosure, wherein like numerals represent like elements. FIGS. 9-13 illustrate a flow governor 201 according to another embodiment of the present disclosure that employs a different internal support structure; and FIG. 14 illustrates a flow governor 301 according to yet another embodiment of the present disclosure. The flow governors of FIGS. 9-14 share many of the same elements, features, and functions as the flow governor 101 of FIGS. 3-8. Reference is made to the description above accompanying FIGS. 3-8 for a more complete description of the features and elements (and alternatives to such features and elements) of the embodiments illustrated in FIGS. 9-14. Any of the features described above with respect to FIGS. 3-8 can be applied to the embodiments of FIGS. 9-14, and vice versa.

Figure 9:
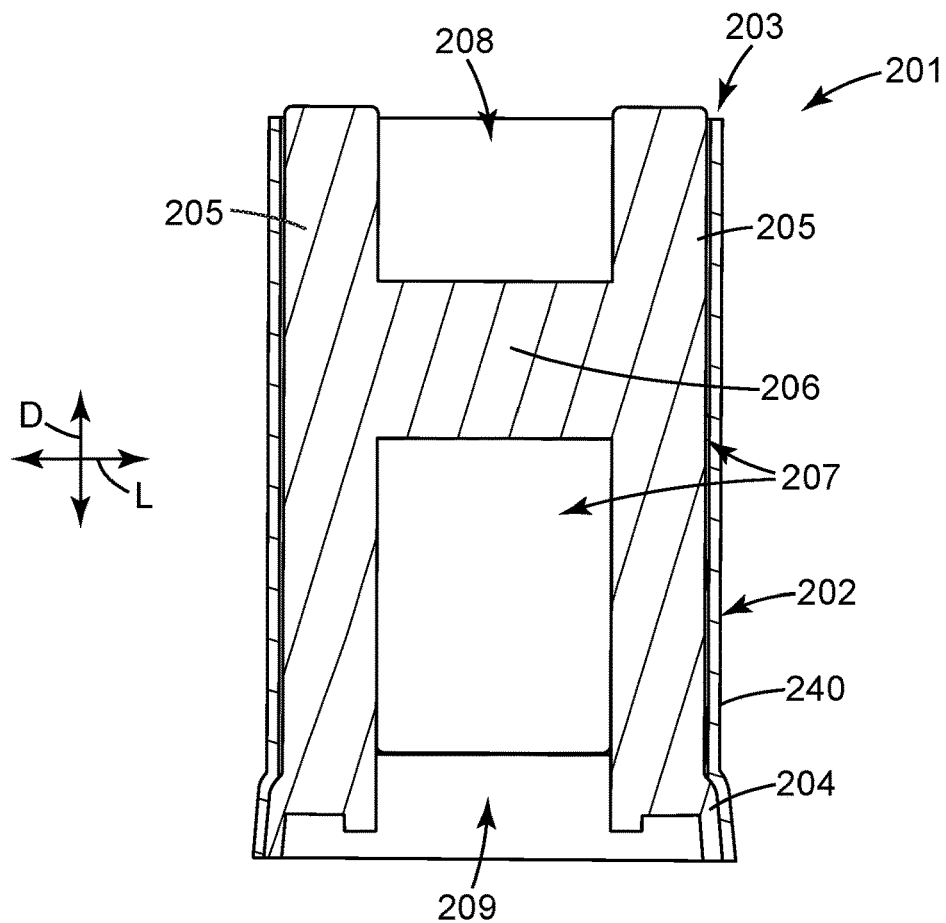
FIG. 9 is a front longitudinal cross-sectional view of a flow governor according to another embodiment of the present disclosure, shown at rest.
Figure 10:
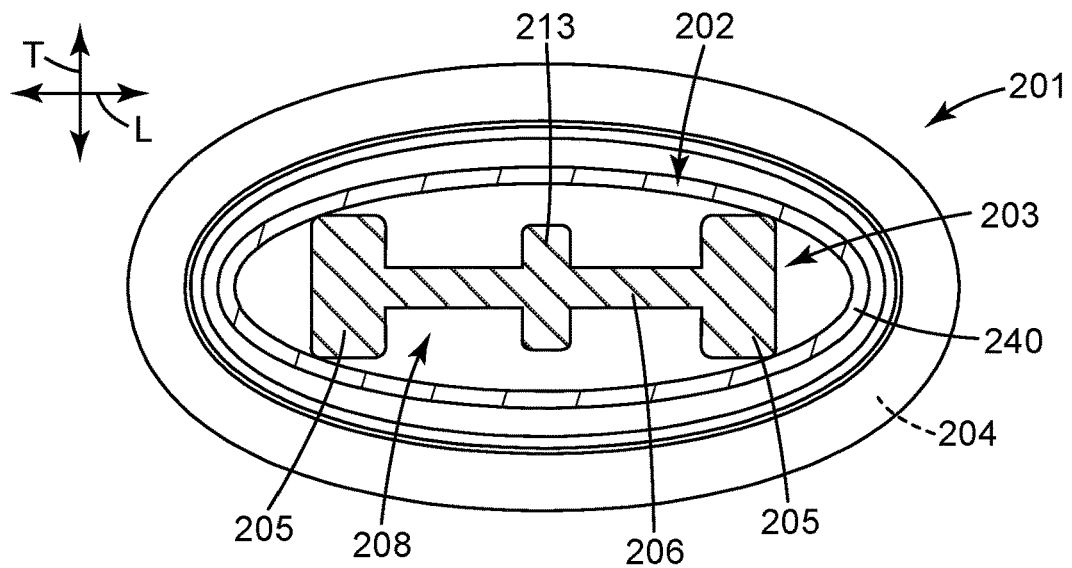
FIG. 10 is a transverse cross-sectional view of the flow governor of FIG. 9, shown at rest.

With reference to FIGS. 9-13, the flow governor 201 includes a tubular element 202 comprising at least one flexible wall 240, and an internal support structure 203. In this embodiment, the internal support structure 203 includes a hollow base 204, solid pillars 205 (i.e., with no lumens), a cross member 206, and one or more splines (or transverse protrusions or transverse splines) 213 (see FIGS. 10 and 12) protruding from the cross member 206 (e.g., protruding transversely from the laterally oriented cross member 206). In some embodiments, as shown, the one or more transverse protrusions 213 can be located laterally centrally with respect to the internal support structure 203 and protruding forwardly and rearwardly with respect to the cross member 206 (i.e., when viewed in transverse cross-section, as shown in FIG. 10). In some embodiments, the one or more transverse protrusions 213 can protrude from the internal support structure 203 substantially orthogonally with respect to the at least one flexible wall 240 of the tubular element 202.

Figure 12:
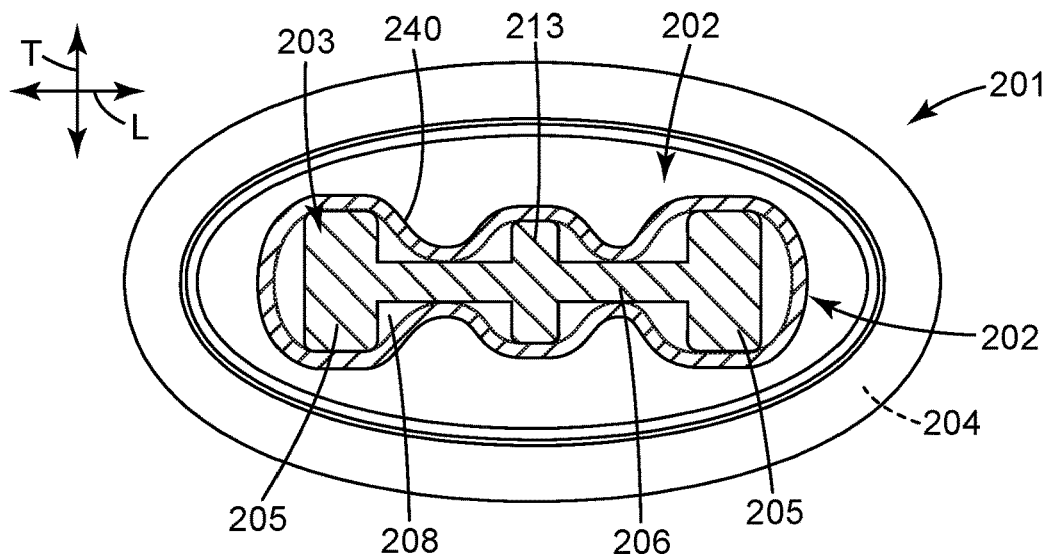
FIG. 12 is a transverse cross-sectional view of the flow governor of FIGS. 9-11, shown in operation.

By way of example only, the internal support structure 203 has an "H" shaped longitudinal cross-sectional shape (i.e., taken along the longitudinal direction D), as shown in FIG. 9 and a generally "H" shaped transverse cross-sectional shape (i.e., taken substantially orthogonally with respect to the longitudinal direction D, e.g., in a lateral-transverse plane), as shown in FIGS. 10 and 12.

Furthermore, in embodiments employing at least one transverse protrusion 213, the internal support structure 203 can further include a transverse cross-sectional shape including at least one capital English letter "E." Particularly, in embodiments employing two laterally-centered transverse protrusions 213, as shown in FIGS. 10 and 12, the internal support structure 203 can have a transverse cross-sectional shape including two capital letter "E"s, merged back-to-back and oriented with the long side of the "E" in the lateral direction L. Unlike the hollow pillars 105 of FIGS. 3-8, the solid pillars 205 lack any internal lumen with long aspect ratios, and therefore have a geometry that may be more desirable for ease of manufacture. Other arrangements, not necessarily "H"-shaped in longitudinal or transverse cross-section, will also be apparent to one skilled in the art. Examples include flow governors having one or more internal support structures having transverse cross-sectional shapes including, or similar to, any of the letters selected from the English capital letters of B, C, D, E, H, M, N, O, S, V, W, X and Z. Other shapes will also be apparent to one of ordinary skill in the art.

Figure 11:
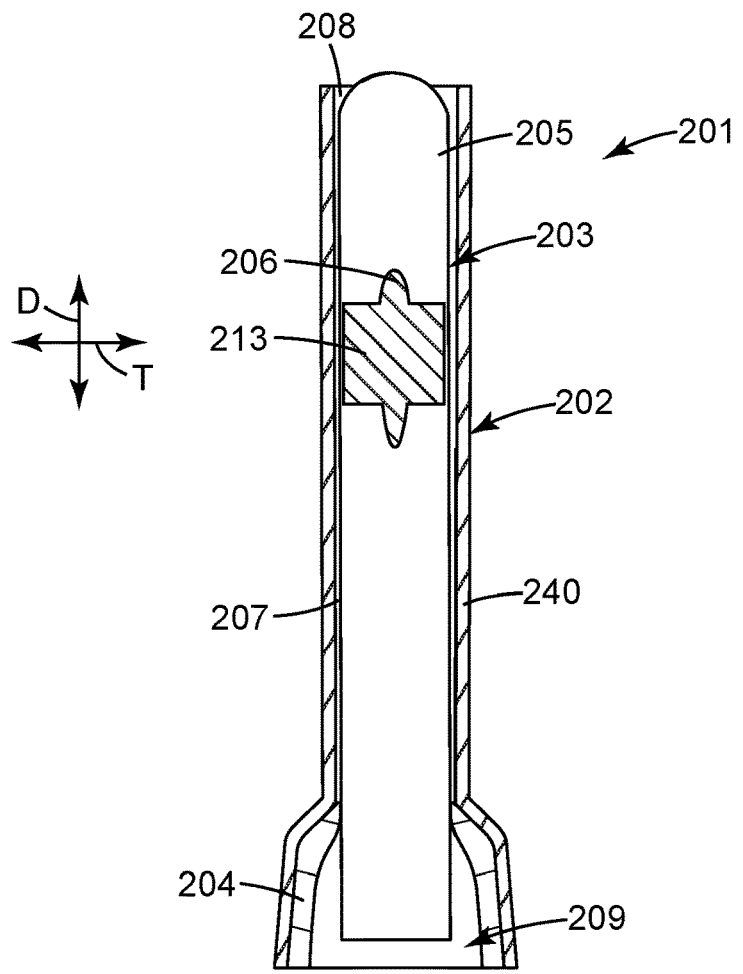
FIG. 11 is a side longitudinal cross-sectional view of the flow governor of FIGS. 9-10, shown at rest.
Figure 13:
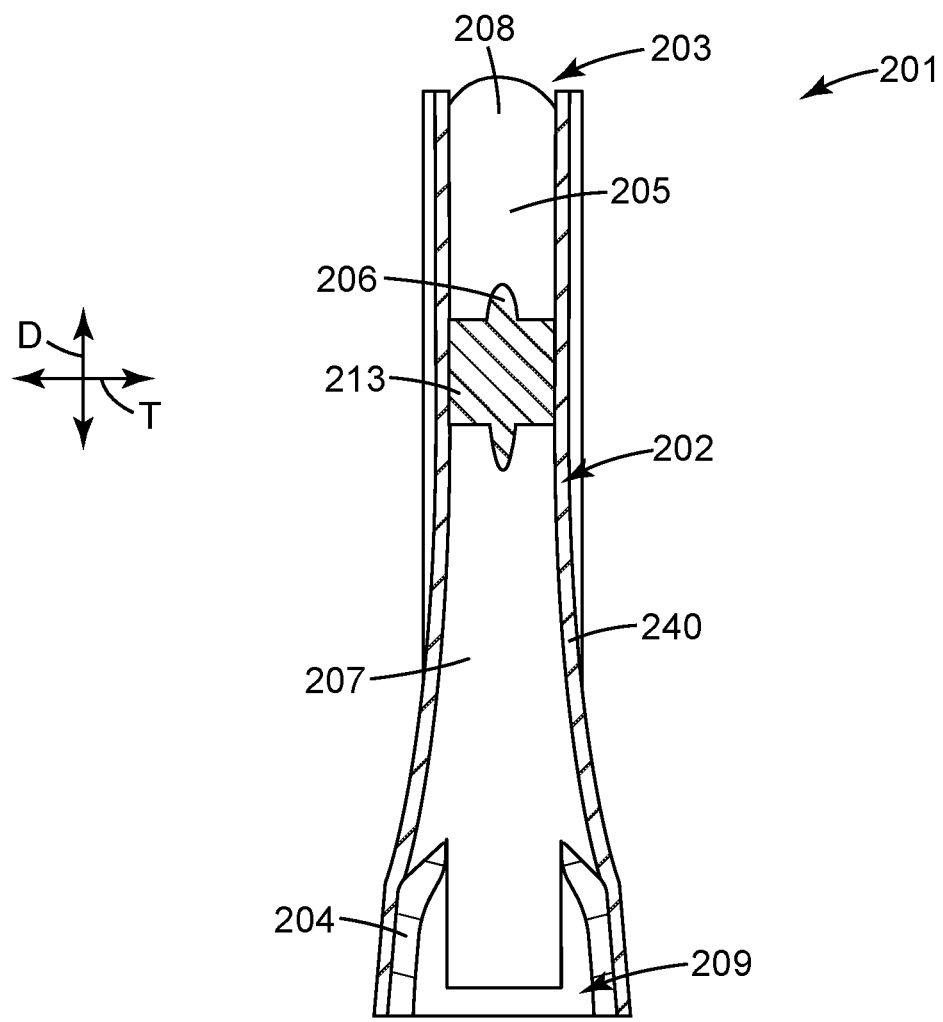
FIG. 13 is a side longitudinal cross-sectional view of the flow governor of FIGS. 9-12, shown in operation.
Figure 14:
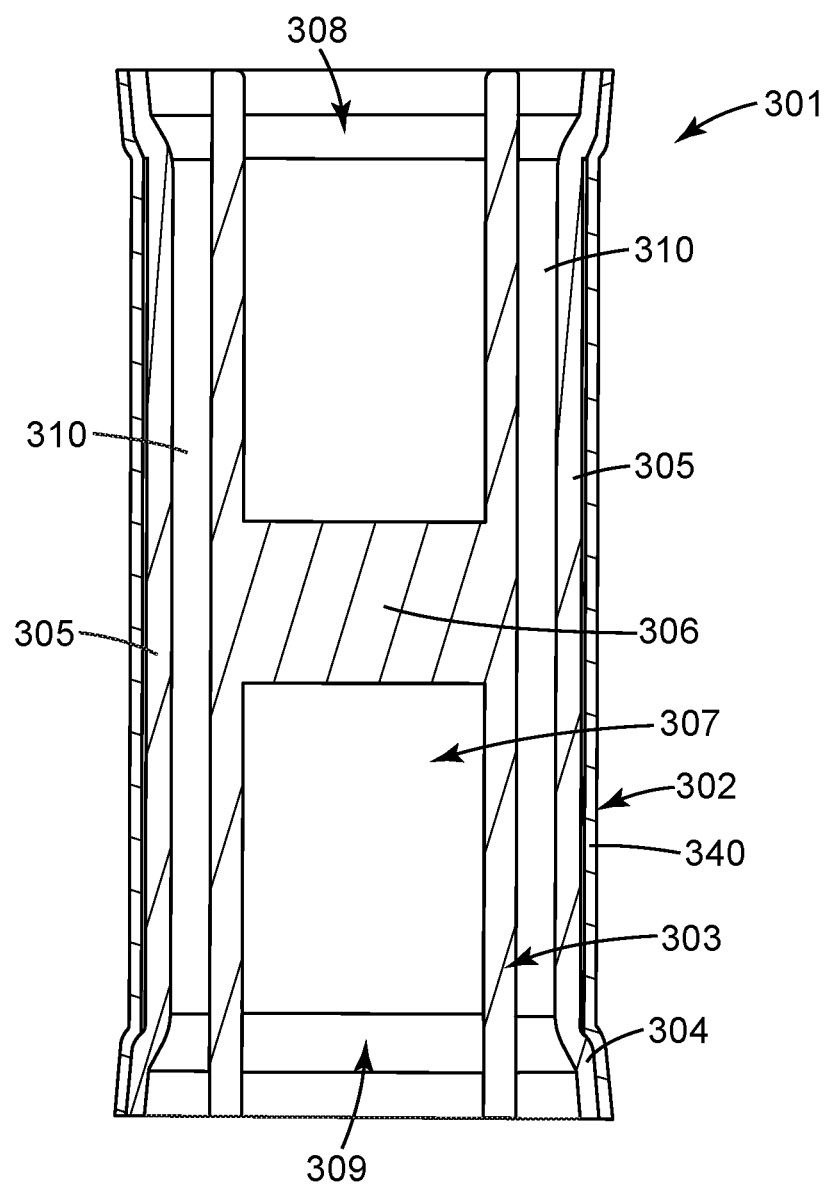
FIG. 14 is a front longitudinal cross-sectional view of a flow governor according to another embodiment of the present disclosure.

FIGS. 9-11 illustrate the flow governor 201 at rest (i.e., with the tubular element 202 in an uncollapsed state), and FIGS. 12-13 illustrate the flow governor 201 in an operative state (i.e., with the tubular element 202 in a collapsed state).

The flow governor 201 includes an air flow path 207 formed between the internal support structure 203 and the tubular element 202, the air flow path 207 including an air inlet 208 and air outlet 209. FIG. 10 shows a transverse cross-section of the flow governor 201, taken generally perpendicularly with respect to the general direction of air flow, which illustrates that the tubular element 202 has an approximately elliptical transverse cross-sectional shape at rest. In some embodiments, as shown, the splines 213 protrude outwardly from the cross member 206 (e.g., in the transverse direction T) less than the solid pillars 205 do. In alternative embodiments, the splines can be dimensioned to protrude an equal distance from the cross member 206 as the solid pillars 205, or alternatively, can protrude further. Alternatively, each solid pillar 205 can have a transverse cross-sectional shape in the form of a cross rather than an approximate rectangle. Many more variants to the cross-sectional shape and dimensions of the internal support structure 203 are possible, as will be apparent from these examples. Each variant will have its own air flow characteristics as a function of pressure drop and air flow rate, in combination with the characteristics of the form and material of the tubular element 202.

FIG. 11 illustrates that the tubular element 202 and the solid pillars 205 are oriented generally parallel to the longitudinal direction D, and that the tubular element 202 is not in contact with the solid pillars 205 at rest, and that the pillars protrude from the tubular element 202 at the air inlet 208 (i.e. protrude from an upstream end of the tubular element 202.

FIGS. 12 and 13 illustrate the flow governor 201 in an operative state. When air is sucked through the air outlet 209, it flows into the air flow path 207 via the air inlet 208. As shown, the reduced air pressure created by the patient's inhalation causes a reduction in diameter along the minor axis of the elliptically sectioned tubular element 202 resulting in inward bending as shown in FIG. 12. As the tubular element 202 is supported at the downstream end by the hollow base 204, inward bending occurs predominantly at the end of the tubular element 202 that is nearer to the air inlet 208, the inward bending restricting the cross-sectional area of the air flow path 207. The lower the air pressure in the air flow channel 207, the greater the inward deformation of the tubular element 202 and hence, the greater the reduction in the cross-sectional area of the air flow path 207 and the greater the resistance to air flow.

Complete collapse of the elliptical cross-sectioned tubular element 202 is prevented by the solid pillars 205. These structures, along with the cross member 206, provide structural support that prevents significant reduction in the diameter along the major axis of the elliptically sectioned tubular element 202. The splines 213 additionally provide support along the minor axis, preventing the tubular element 202 (and particularly, the at least one flexible wall 240) from collapsing too tightly onto the cross member 206. Residual air flow is thus always possible via the residual air flow channel gaps, no matter how great the patient's inspiratory pressure drop.

FIG. 14 illustrates a flow governor 301 according to another embodiment of the present disclosure. The flow governor 301 includes a tubular element (or "tube") 302 comprising at least one flexible wall 340, and an internal support structure 303 that is dimensioned to be received within the tubular element 302 (i.e., within the at least one flexible wall 340). The tubular element 302 surrounds and envelopes the internal support structure 303. The internal support structure 303 consists of a hollow base 304, two hollow pillars 305 (each comprising a lumen 310), and a cross member 306. As shown in FIG. 14, in some embodiments, the tubular element 302 can be anchored or otherwise attached (e.g., to the internal support structure 303) at both ends, rather than being free at the air inlet end. As shown in FIG. 14, in some embodiments, the cross member 306 can be located longitudinally centrally with respect to the pillars 305. As a result, in addition to the lateral and transverse symmetries of previous embodiments, the internal support structure 303 (and the flow governor 301) can also have longitudinal symmetry (e.g., about a central lateral-transverse plane).

As with previous embodiments, the outer diameter of the hollow base 304 is larger than the inner diameter of the flexible tubular element 302, and assembly of the two components is achieved by stretching the tubular element 302 over the outer surface of the hollow base 304. The tubular element 302 and the internal support structure 303 together define an air flow path 307 therebetween that includes an air inlet 308 and an air outlet 309. The air flow path 307 also includes the lumens 310 through the pillars 305. When air is sucked towards the air outlet 309, it flows into the air flow path 307 and through (i.e., via) the lumens 310 and around the pillars 305 via the air inlet 308, creating a reduction in air pressure in the air flow path 307 by the Bernoulli Effect. The reduced pressure in the air flow path 307 causes a reduction in the diameter along the minor axis of the elliptical cross-section of the tubular element 302 centered at approximately the midpoint of the air flow path 307.

One possible advantage of having the tubular element 302 secured at both ends is that the tubular element 302 can be of greater thickness for a given flow governing performance, thereby offering a manufacturing advantage with regard to the dimensional specification range of the tubular element 302. Another possible advantage of having the tubular element 302 secured at both ends is that the use of a symmetrical arrangement (e.g., symmetrical longitudinally, laterally and transversely) can offer a manufacturing benefit, as it does not require a consistent and specified end-to-end orientation during assembly.

Medicinal Inhalers

Figure 15:
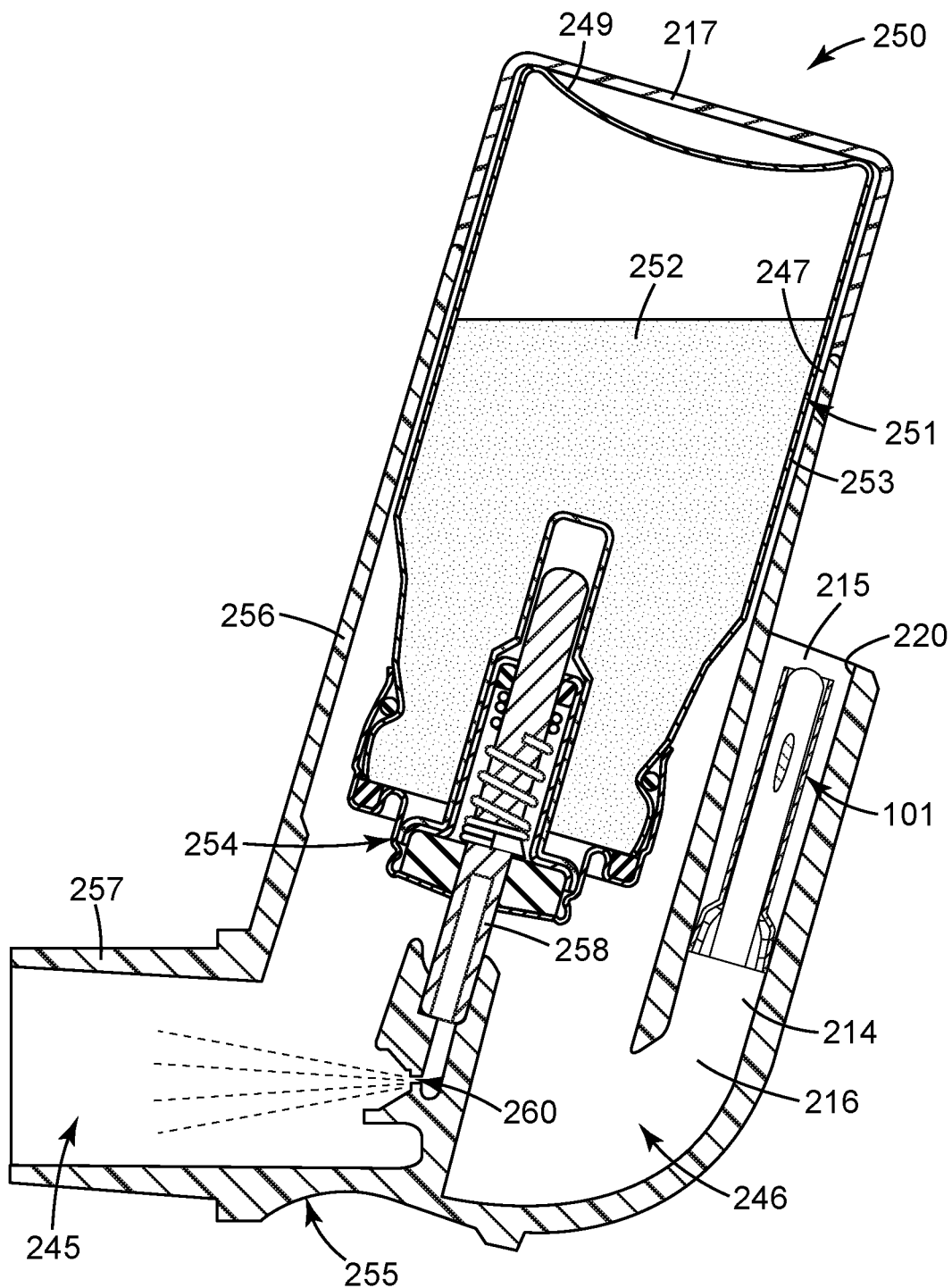
FIG. 15 is a side cross-sectional view of a medicinal inhaler according to one embodiment of the present disclosure, comprising the flow governor of FIGS. 3-8 located in a dedicated air flow path and a cover over an open end of a housing that receives a medicament canister.

FIG. 15 illustrates a medicinal inhaler 250 according to one embodiment of the present disclosure that employs a flow governor 101 of the present disclosure. By way of example only, the medicinal inhaler 250 is shown in FIG. 15 as including the flow governor 101 of FIGS. 3-8; however, it should be understood that any flow governor of the present disclosure can be employed in the inhaler 250. By way of further example, the medicinal inhaler 250 is shown as being a press-and-breathe pressurized metered dose inhaler (pMDI).

The inhaler 250 shares many of the elements, features, and functions of the pMDI 50 of FIG. 1, wherein like numerals represent like elements. As a result, reference is made to the description above accompanying FIG. 1 for a more complete description of the features and elements (and alternatives to such features and elements) of the inhaler 250 of FIG. 15.

The inhaler 250 includes a canister 251 containing a medicament formulation 252, the canister comprising a can 253 sealed with a metering valve 254. The canister 251 sits within a housing (or "actuator") 255 comprising an initially open tubular sleeve portion 256 having a first open end 247 dimensioned to receive the canister 251 and from which its base 249 can protrude, and a portion in the form of an open tubular mouthpiece 257. The open housing 255 can define an air flow path 246 therein, in particular from an air inlet 215, open to ambience, to the mouthpiece 257 that defines an inhalation orifice or an air outlet 245. A stem portion 258 protrudes from the metering valve 254 and is located and retained by friction in a stem socket 259 formed as an integral part of the housing 255. A spray orifice 260 is formed in the stem socket 259, and provides a passage for fluid communication between the valve stem portion 258 and the mouthpiece 257.

As further shown in FIG. 15, the inhaler 250 further includes the flow governor 101 incorporated directly into the inhaler 250 by being positioned in the air flow path 246 of the inhaler 250. Particularly, in the embodiment of FIG. 15, the flow governor 101 is located in a dedicated tubular air flow path 214 between the air inlet 215 and an air outlet 216 in fluid communication with the air outlet 245 of the inhaler 250, such that the air flow path 214 forms a portion of the overall air flow path 246 of the inhaler 250.

By way of example only, the dedicated air flow path 214 is located at a rear portion of the housing 255 (i.e., opposite the mouthpiece 257) and is integrally formed with the housing 255. By way of further example, the air inlet 215 is defined by a second open end 220 of the housing 255, wherein the second open end 220 is dimensioned to receive the flow governor 101. As a patient inhales on the mouthpiece 257, air flows via the air inlet 215 into the flow governor 101, creating the reduced pressure required to activate the flow governor 101, thus regulating the air flow. In order to avoid any ingress of air from the top of the inhaler 250 that would bypass the flow governor 101, a cover 217 that forms a seal is located over the first open end 247 of the housing 255. The cover 217 can be flexible, in order to allow the base 249 of the canister 251 to still be depressed to deliver the dose of medicament formulation. This flexibility can be provided via appropriate choice of material(s) of manufacture for the cover 217, via the cover geometry and design, or both.

The dedicated air flow path 214 is shown as being substantially constant in cross section in FIG. 15; however, this need not be the case. Various possible shapes and configurations for air flow paths including a flow governor of the present disclosure and for being incorporated into a medicinal inhaler of the present disclosure are described in greater detail below with reference to FIGS. 20-23.

Figure 16:
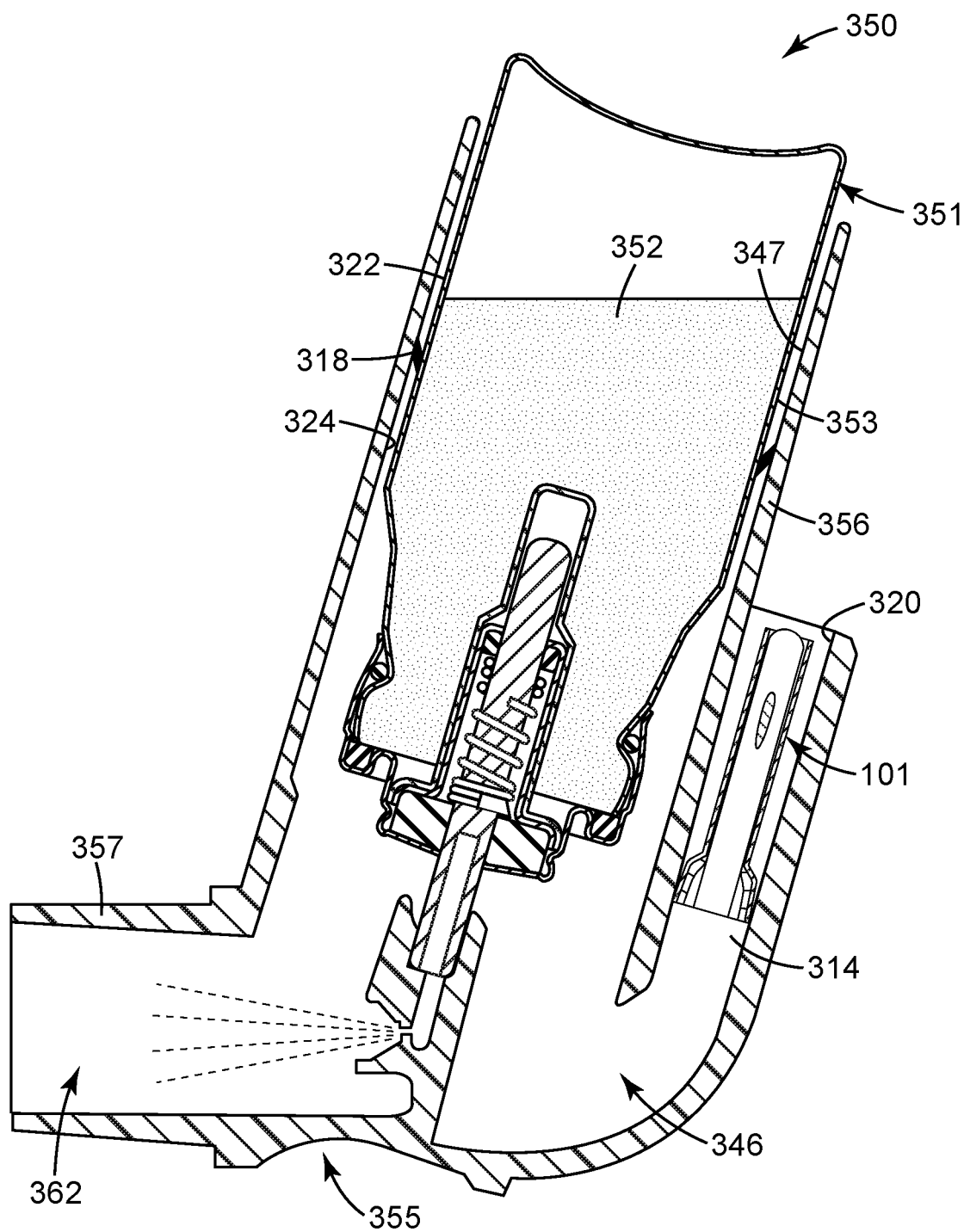
FIG. 16 is a side cross-sectional view of a medicinal inhaler according to another embodiment of the present disclosure, comprising the flow governor of FIGS. 3-8 located in a dedicated air flow path and a skirt seal located between a medicament canister and a housing that receives the canister.

FIG. 16 illustrates a medicinal inhaler 350 according to another embodiment of the present disclosure. The inhaler 350 shares many of the elements, features, and functions of the inhalers 50 and 250 of FIGS. 1 and 15, respectively, wherein like numerals represent like elements. As a result, reference is made to the description above accompanying FIGS. 1 and 15 for a more complete description of the features and elements (and alternatives to such features and elements) of the inhaler 350 of FIG. 16.

The inhaler 350 includes a housing 355 that defines an air flow path 346 therethrough, including an open end 320 and an air outlet 345 (formed by a mouthpiece 357). The housing 355 also includes an initially open tubular sleeve portion 356 having an open end 347 dimensioned to receive a canister 351 comprising a medicament formulation 352. The inhaler 350 further includes the flow governor 101 (i.e., by way of example only) positioned in the air flow path 346 extending from the open end 320 to the air outlet 345. Particularly, similar to the embodiment of FIG. 15, the flow governor 101 is positioned in a dedicated air flow path 314 that is open to ambience (e.g., via the open end 320) and in fluid communication with, and forms a portion of, the overall air flow path 346 of the inhaler 350. In addition, the dedicated air flow path 314 is integrally formed with the housing 355, and particularly is formed in a rear portion of the housing 355, i.e., opposite the mouthpiece 357.

FIG. 16 illustrates an alternative system for sealing the open end 347 of the housing 355 of the inhaler 350 to avoid bypass air 'defeating' the flow governor 101. In this embodiment, a skirt seal 318 is used to seal or substantially seal the gap around the canister 351. That is, the skirt seal 318 is located between an outer surface 322 of the canister 351 (and particularly, an outer surface 322 of a can 353 of the canister 351) and an inner surface 324 of the housing 355 (and particularly, an inner surface 324 of the sleeve portion 356 of the housing 355) to seal the open end 347 (i.e., the sleeve portion 356 of the housing 355) from ambience.

The skirt seal 318 can be formed of a thin and flexible annular elastomer and can be made sufficiently flexible to avoid introducing any great resistance to longitudinal canister movement in the sleeve portion 356 of the housing 355. Other arrangements of sealing components will be apparent to one skilled in the art.

Figure 17:
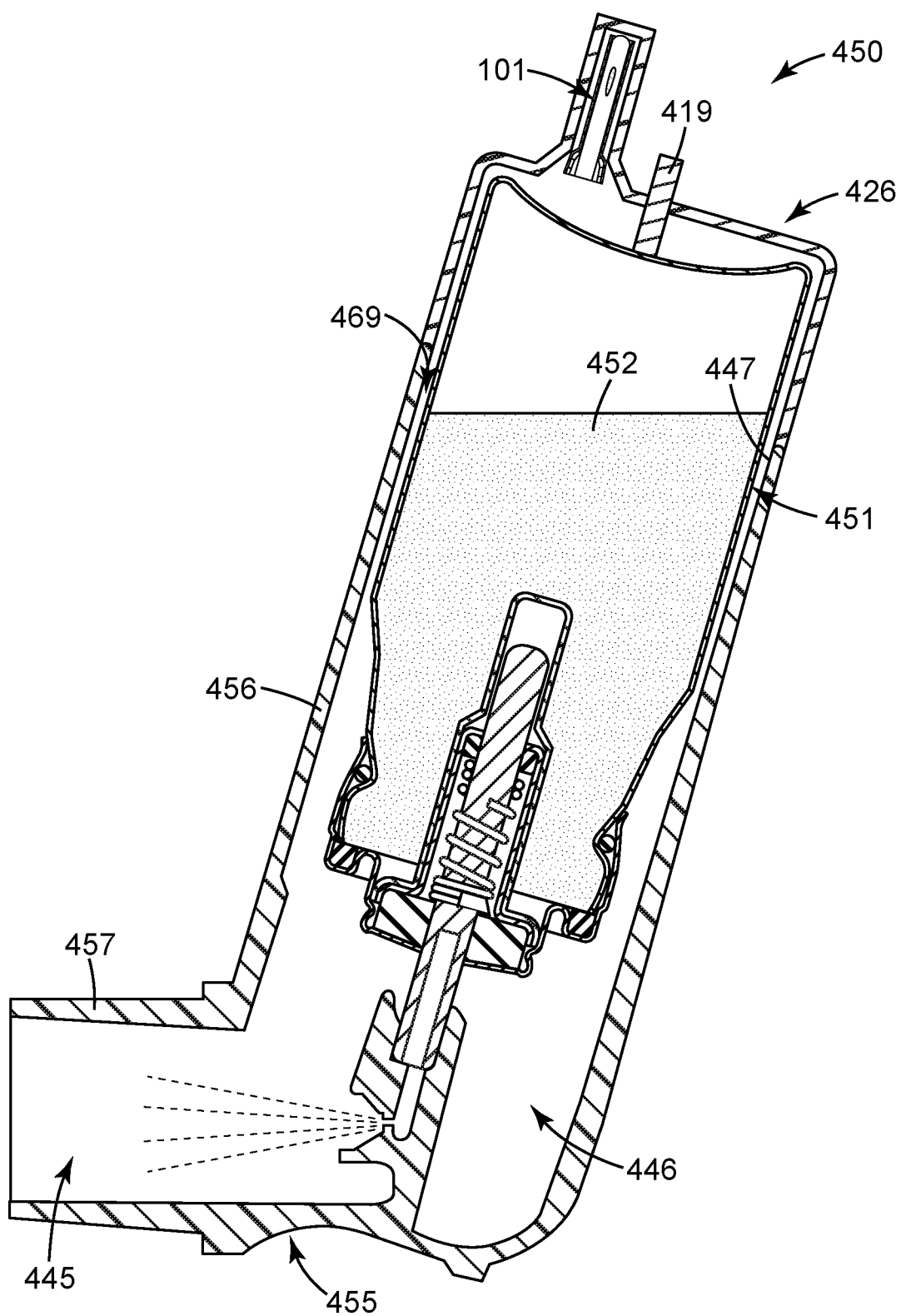
FIG. 17 is a side cross-sectional view of a medicinal inhaler according to another embodiment of the present disclosure, comprising the flow governor of FIGS. 3-8 located in a cap configured to be coupled to an open end of a housing that receives a medicament canister.

FIG. 17 illustrates a medicinal inhaler 450 according to another embodiment of the present disclosure. The inhaler 450 shares many of the elements, features, and functions of the inhalers 50 and 250 of FIGS. 1 and 15, respectively, wherein like numerals represent like elements. As a result, reference is made to the description above accompanying FIGS. 1 and 15 for a more complete description of the features and elements (and alternatives to such features and elements) of the inhaler 450 of FIG. 17.

The inhaler 450 includes a housing 455 that defines an air flow path 446 therethrough, including an air passage 469 and an air outlet 445. Particularly, the housing 455 includes an open tubular sleeve portion 456 having an initially open end 447 that defines the air passage 469, and a mouthpiece 457 that defines the air outlet 445. The sleeve portion 456 and the open end 447 are dimensioned to receive a canister 451 comprising a medicament formulation 452. The inhaler 450 further includes the flow governor 101 (i.e., by way of example only) positioned in the air flow path 446.

FIG. 17 illustrates another alternative system for sealing the open end 447 of the housing 455 of the inhaler 450 to avoid bypass air 'defeating' the flow governor 101. In this embodiment, rather than having the flow governor 101, or a dedicated air flow path, form a portion of or be built into the housing 455 of the inhaler 450, the flow governor 101 is located in a cap 426 configured to be coupled to (e.g., clipped or snapped onto) the initially open end 447 of the housing 455 to close and seal the open end 447, such that the cap 426 ends up forming a portion of the air flow path 446 when coupled to the housing 455. As a result, the cap 426, when coupled to the housing 455, defines the air inlet of the air flow path 446 of the inhaler 450, such that inhaled air must pass through the flow governor 101 in the cap 426. In this embodiment, the cap 426 can be provided as a retrofitted accessory to an existing inhaler.

Similar to the cover 217 of FIG. 15, the cap 426 can be formed of a flexible material to allow the canister 451 to still be pressed when desired. In addition, or alternatively, as shown in FIG. 17, in some embodiments, the inhaler 450 can include a button 419 to allow the canister 451 to be pressed to release a dose of medicament. For example, in some embodiments, the button 419 can be fixed with respect to the cap 426, and the cap 426 can be flexible. In some embodiments, the cap 426 need not be flexible, and the button 419 can be movable with respect to the cap 426.

In other embodiments, the flow governors of the present disclosure can be built into other locations within an inhaler. For example, the flow governor could be positioned below the foot of the stem socket (see, e.g., the stem socket 59 of FIG. 1) into which the valve stem portion (see, e.g., the stem portion 58 of FIG. 1) of the canister (see, e.g., the canister 51 of FIG. 1) locates. In such embodiments, e.g., its inlet can be positioned below the mouthpiece of the inhaler (see, e.g., the mouthpiece 57 of FIG. 1), and its outlet could be arranged to feed air to the stem socket region. A sealing cover (see, e.g., the cover 217 of FIG. 15), a skirt seal (see, e.g., the skirt seal 318 of FIG. 16), or another sealing means can be employed over the open end of the housing that receives the canister of medicament to avoid any air bypassing the flow governor.

In any of the inhalers of the present disclosure employing flow governors of the present disclosure, grill structures can be provided over the air inlet of the air flow path in which the flow governor is located, such that large pieces of debris, for example, are not inadvertently taken into the inhaler device. Furthermore, in each embodiment of the inhaler of the present disclosure, the air inlet of the flow governor air flow path is preferably positioned where it will not readily be inadvertently blocked or obstructed by a patient's lips, fingers, etc., during use.

Figure 18:
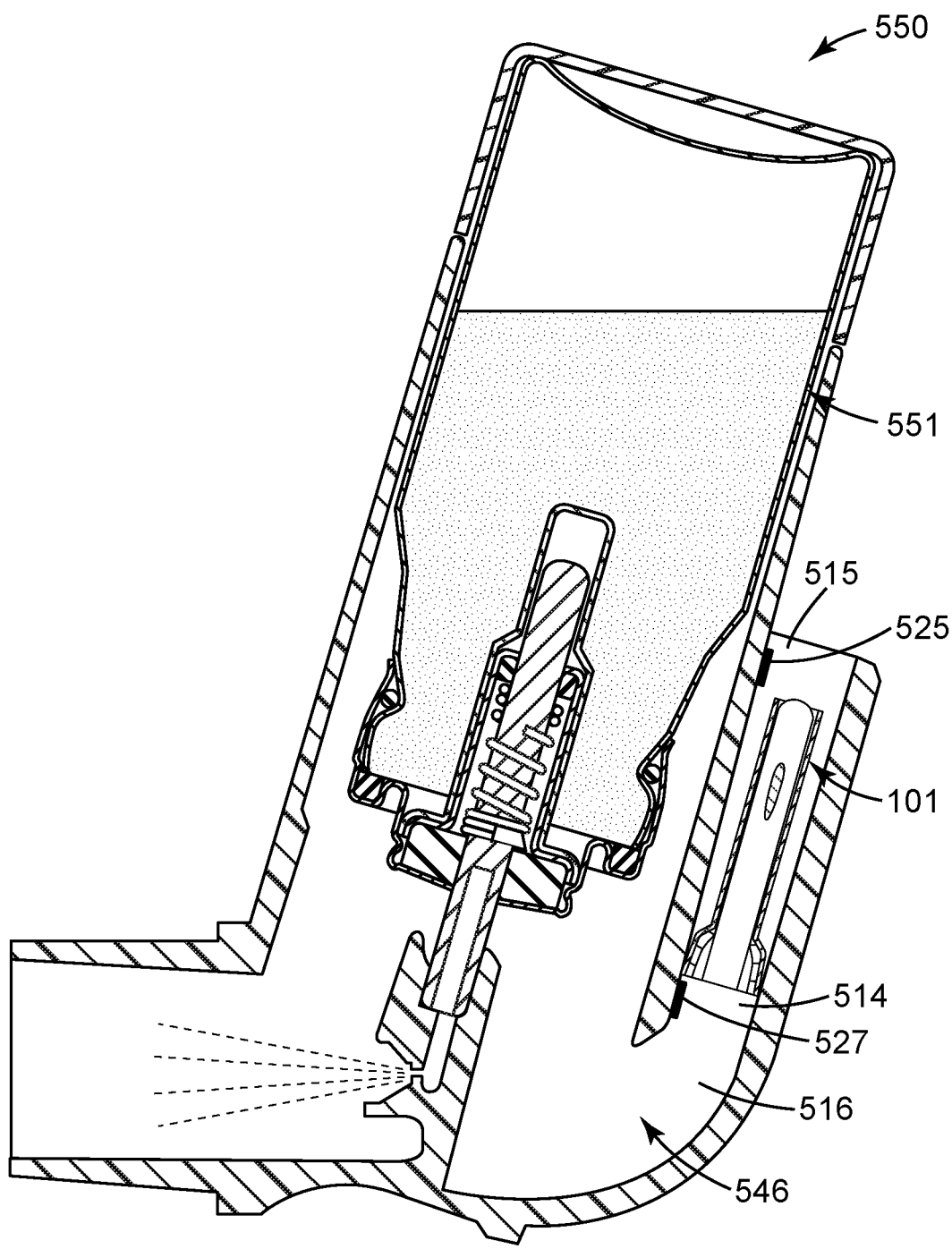
FIG. 18 is a side cross-sectional view of a medicinal inhaler according to another embodiment of the present disclosure, comprising the flow governor of FIGS. 3-8 located in a dedicated air flow path and one or more pressure sensors in fluid communication with the dedicated air flow path.

FIG. 18 illustrates a medicinal inhaler 550 according to another embodiment of the present disclosure. By way of example only, the inhaler 550 is substantially the same as the inhaler 250 of FIG. 15 and includes the flow governor 101 positioned in the air flow path 546 of the inhaler, except that the inhaler 550 further includes one or more pressure sensors 525, 527 located in the dedicated flow governor air flow path 514. Reference is made to the description above accompanying FIG. 15 for a more complete description of the features and elements (and alternatives to such features and elements) of the inhaler 550 of FIG. 18.

As shown in FIG. 18, a pressure sensor 525 is located in fluid communication with the dedicated air flow path 514. The pressure sensor 525 is connected to a controller (not shown), both of which are powered by a suitable power source (not shown) with an appropriate switch to provide a power on/off function.

Generally, a controller of the present disclosure can be a suitable electronic device, such as, for example, a programmable logic controller ("PLC"), a programmable circuit board ("PCB"), a microprocessor, and/or other suitable devices or structures. As such, the controller 151 may include both hardware and software components, and the term "controller" is meant to broadly encompass the combination of such components.

With continued reference to FIG. 18, when the power is switched on, the pressure sensor 525 determines the atmospheric pressure. When the patient inhales air through the inhaler 550, causing air to flow out of the air outlet 516, air flows into the air flow path 514 via the air inlet 515, and the pressure sensor 525 detects and/or measures the dynamically changing air pressure brought about by the patient's inspiratory effort in conjunction with the functionality of the flow governor 101.

Detection of pressure changes, relative to the initial atmospheric pressure, via cooperation between the pressure sensor 525 and a controller, can be used to calculate the air flow rate past the pressure sensor 525. (The air flow rate causes a reduction in local air pressure, via the Bernoulli Effect.) When a desired pre-determined flow rate is reached, an electronic signal can be sent to a suitable component, such as a Light Emitting Diode (LED) or Liquid Crystal Display (LCD) or audio speaker, to provide a cue for the user to actuate the inhaler 550. Alternatively, the electronic signal could be used to enable a mechanism to automatically actuate the inhaler 550.

Furthermore, in some embodiments, a second pressure sensor 527 can be included in the air flow path 514 towards the air outlet 516. The presence of this second pressure sensor 527 can be used to determine air flow direction via comparison (e.g., performed by the controller) of the relative local air pressures at the two pressure sensors 525, 527, which can be used to distinguish inspiration from exhalation (e.g., if a patient blows into the inhaler 550 instead of sucking air through the inhaler 550). This can allow a linked breath-actuation triggering mechanism (e.g., mechanical or electronic) to be arranged not to operate if the patient breathes out into the inhaler, rather than in through it, the two breathing modes being easily differentiated by the different relative pressure drop relationships detected by the first and second sensors 525 and 527.

Inclusion of two pressure sensors 525, 527 in fluid communication with the air flow path 514 enables measurement (in conjunction with the appropriate electrical components, such as a controller (e.g., a programmable circuit board (PCB)), a power source, etc.) of pressure changes, which can be correlated with air flow rates. When a predetermined flow rate is achieved, this can prompt a signal to trigger an electrical firing mechanism to actuate the inhaler canister 551. Such a mechanism can negate the requirement for the patient to coordinate inhaling and actuating the inhaler. In addition, the triggering flow rate can be programmed differently for different products. In each case, though, use of an integral flowmeter (which the pressure sensors 525, 527 can effectively be) and electronic actuation can ensure that the inhaler 550 can be actuated at an appropriate time in the patient's inspiratory maneuver. The electronic circuitry involved can also be configured to allow each triggering event to be counted and recorded, and can be used to also provide a dose count, e.g. for display to the patient of the theoretical number of doses thus still remaining.

As well as using the pressure measurements and the calculated flow rate data to trigger canister actuation, such a system can optionally be configured to provide feedback to the patient and to their physician.

The air flow path 514 containing the flow governor 101 can be incorporated, in a similar fashion as already described, into any of the variety of inhalers mentioned above. It should also be understood that the incorporation of pressure sensors in the flow governor air flow path can be employed in any inhaler, such as that of any of FIGS. 15-17, or any other inhaler of the present disclosure. By way of example, the pressure sensors of FIG. 18 can be positioned in an air flow path formed in the cap 426 of FIG. 17. The relevant electronic componentry can also be incorporated into the cap 426.

In some embodiments, no matter which type of inhaler is employed, the air flow path 514 including the flow governor 101 and the pressure sensors 525, 527, along with the relevant electrical components, can be manufactured as a separate part or component, or as a portion of the inhaler 550. FIGS. 20-23, described below, illustrate exemplary flow governor assemblies (or "air flow paths" or "air flow path assemblies") of the present disclosure comprising flow governors of the present disclosure that can be separately formed and put in fluid communication with or otherwise incorporated into an inhaler, or that can form a portion of an inhaler of the present disclosure.

Figure 19:
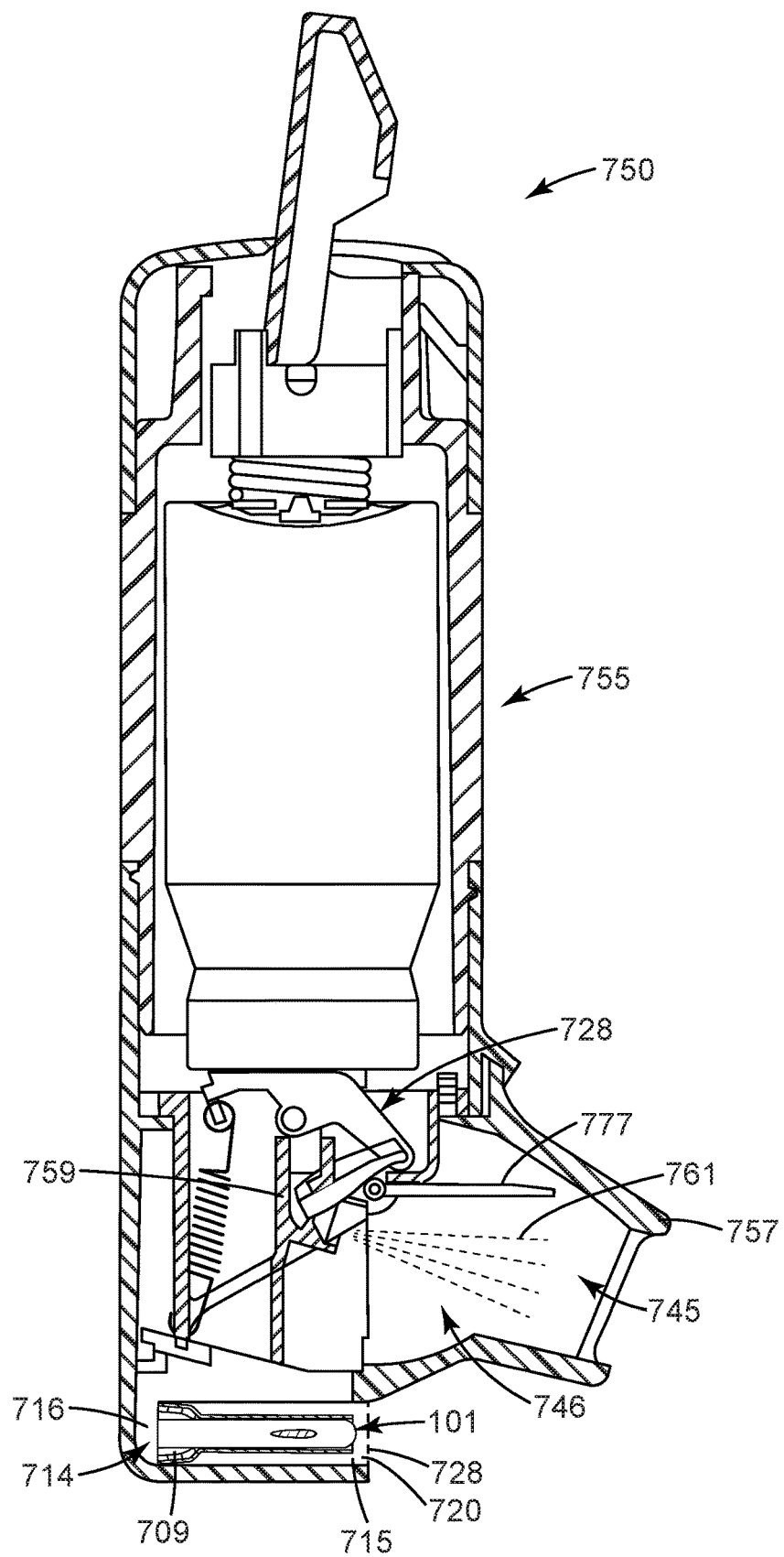
FIG. 19 is a side cross-sectional view of a breath-actuated medicinal inhaler according to one embodiment of the present disclosure, comprising the flow governor of FIGS. 3-8 located in a dedicated air flow path.

FIG. 19 illustrates an inhaler 750 according to another embodiment of the present disclosure, including the flow governor 101 of FIGS. 3-8. By way of example, the inhaler 750 is illustrated as being a variant of an inhaler available under the trade designation AUTOHALER™ from 3M Company, St. Paul, Minn. Additional details regarding the inhaler 750 can be found in U.S. Pat. No. 7,296,567, which is incorporated herein by reference in its entirety.

As shown in FIG. 19, the flow governor 101 is positioned in a dedicated air flow path 714 located in a bottom portion of a housing 755 of the inhaler 750, which is integrally formed with the housing 755. The dedicated air flow path 714 includes an air inlet 715 (e.g., defined by an auxiliary open end 720) open to ambience and an air outlet 716 in fluid communication with an air flow path 746 of the inhaler 750. Particularly, the dedicated air flow path 714 is arranged substantially horizontally, such that the air inlet 715 is located generally below the mouthpiece 757. Sealing means (not shown) are provided to ensure that there are no significant air leak inlets elsewhere in the inhaler 750, in order that substantially all the air flow through the inhaler 750 passes through the dedicated air flow path 714.

In this embodiment, the inspiratory air flow is drawn via the air inlet 715 (e.g., via an inlet grill, screen or grate 728) into the flow governor 101 and thence into the region around a stem socket 759. When the patient inhales on the mouthpiece 757 of the inhaler 750 (which defines an inspiration orifice 745), a vane 777 lifts in the inspiratory air flow, that lifting triggering a mechanical dose release mechanism 728. The emerging medicament formulation spray 761 is entrained in the air flow from the air outlet 709 of the flow governor 101 and the air outlet 716 of the dedicated air flow path 714 and emerges with the air flow via the mouthpiece 757. It will be noted by one skilled in the art that flow governors of the present invention may be positioned in multiple locations in such an inhaler, e.g. at the rear of the inhaler, at the front, on the top, to one side, etc. Additionally, it will be apparent that the outer form of the inhaler can be shaped and styled independently of the internal air flow surfaces.

Again, incorporation of an appropriate electronic memory device could allow capture, storage and retrieval of the patient's inhalation profile (flow rates, pressure drops, etc.) corresponding to each time the inhaler was used. Inclusion of a means to transmit the data, e.g. via a cable or using wireless technology, to a secondary device, e.g. a computer or 'smart' phone, could make these data readily available to the patient's physician or others, in order to allow them to monitor the patient's ability to use the inhaler successfully and to allow appropriate and timely health care advice to be provided based on analysis and interpretation of the retrieved information.

In alternative embodiments, the breath-actuated inhaler can include both a reusable and a replaceable part. For example, a reusable part containing the complex and relatively expensive electronics could be paired in turn with a series of replaceable medicament containing cartridges. In such embodiments, the flow governor can be associated with the replaceable cartridge or, alternatively and preferably, with the reusable unit. In either case, the air flow path of the inhaler can be configured to pass through either the reusable part, the replaceable refill part, or both.

In yet another embodiment, two or more flow governors with differing resistances and/or collapse characteristics can be incorporated into a medicinal inhaler of the present disclosure, or an air flow path of the present disclosure for use with a medicinal inhaler, for example, in a parallel flow path configuration. In a still further embodiment, two or more flow governors with differing resistances and/or collapse characteristics can be incorporated into a medicinal inhaler or air flow path of the present disclosure in a series flow path arrangement. Such embodiments can provide a greater ability to adjust the flow rate versus pressure drop characteristics of medicinal inhalers.

Flow Governor Assemblies

Figure 20:
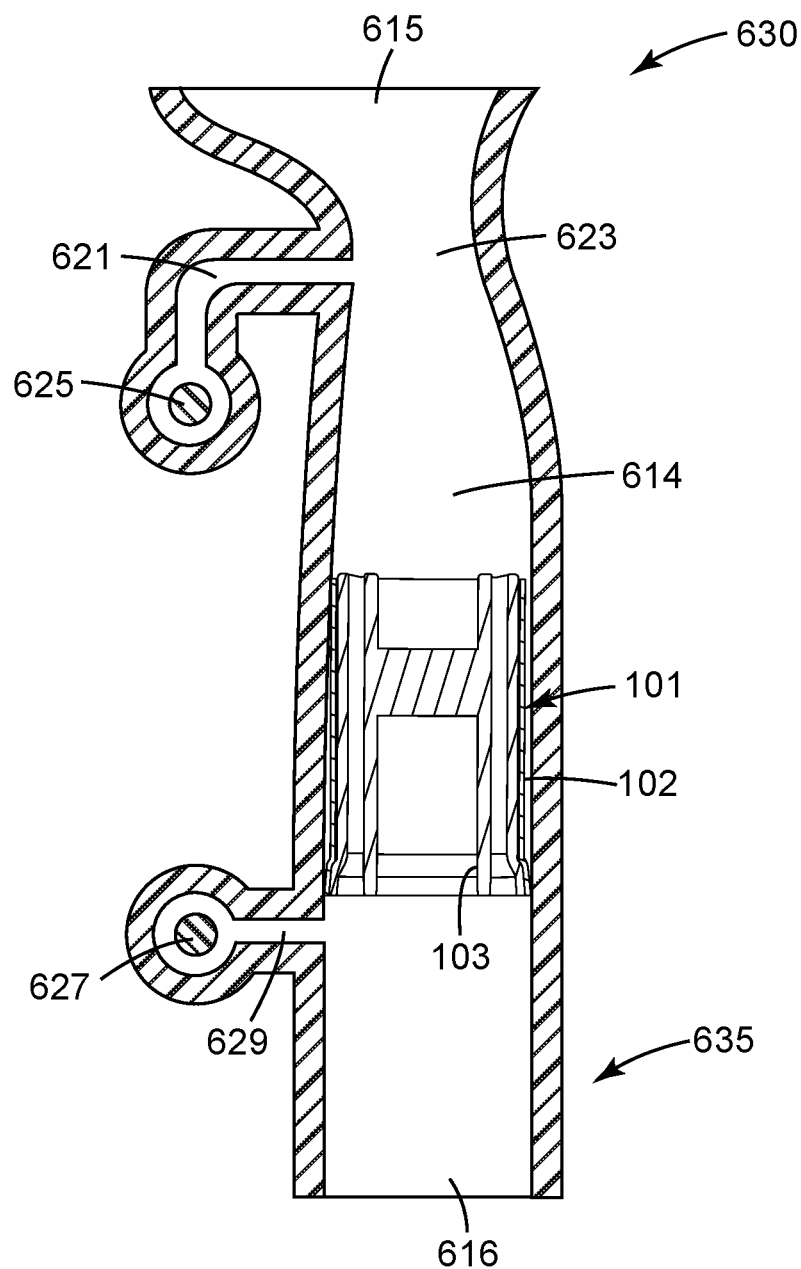
FIG. 20 is a front longitudinal cross-sectional view of a flow governor assembly of a medicinal inhaler according to one embodiment of the present disclosure, comprising the flow governor of FIGS. 3-8, an upstream venturi, and one or more pressure sensors positioned in fluid communication with the flow governor.

FIG. 20 illustrates a flow governor assembly (or "air flow path" or "air flow path assembly") 630 according to one embodiment of the present disclosure. The flow governor assembly 630 can be separately formed and put in fluid communication with or otherwise incorporated into an inhaler, or can form a portion of an inhaler of the present disclosure. As shown in FIG. 20, the flow governor assembly 630 can include a housing 635 that defines an air flow path 614 comprising an air inlet 615 and an air outlet 616; a flow governor 101 positioned in an air flow path 614; and a constriction 623 in the air flow path 614. The housing 635 is shown in greater detail in FIG. 21 and described in greater detail below.

The flow governor 101 can be configured to provide a variable (dynamic) resistance to air flow in an air flow path 614; and the constriction 623 can be configured to provide a fixed (static) resistance to air flow in the air flow path 614. The constriction 623 can include one or more of a venturi section (as shown), a narrow passageway (e.g., a narrow passageway, relative to adjacent regions/portions of the air flow path 614), a tortuous path, and a combination thereof. A tortuous path can include one or more twists, bends or turns (e.g., a sharp turn of at least 60 degrees).

In addition, in some embodiments, the flow governor assembly 630 can further include a first (air inlet) pressure sensor 625, and a second (air outlet) pressure sensor 627. The flow governor assembly 630 can be of dimensions (e.g., a length) appropriate to the physical dimensions of an associated inhaler.

In some embodiments, the housing 635 can be a separate element that can be positioned within, positioned in fluid communication with, and/or coupled to a housing of an inhaler. Additionally, or alternatively, in some embodiments, the housing 635 can refer to a portion of a housing of an inhaler, such that the housing 635 is integrally formed with a housing of an inhaler.

The air flow path 614, and particularly, the air inlet 615 can be shaped to improve the sensitivity of at least the first pressure sensor 625. The first pressure sensor 625 is connected to the air flow path 614 by a first conduit 621. The dimensions of this conduit (e.g., its cross-sectional area) can be chosen to ensure an appropriate balance between having a desirably low pressure drop along its length versus avoiding it being open enough to significantly affect the air flow in the main air flow path 614. In some embodiments, this conduit can be round in cross-section, with an internal diameter of approximately 2 mm and a total internal length of approximately 15 mm.

As mentioned above, the air flow path 614 can further include a fixed or static resistance, particularly, in the form of a constriction (or "venturi constriction") 623 located between the air inlet 615 and the air outlet 616 that particularly forms a venturi tube (or venturi section) that effectively amplifies the local air flow induced pressure drop at the first pressure sensor 625. Particularly, the constriction 623 can be located upstream of the flow governor 101. Such an amplification can enable the use of a less sensitive pressure sensor to measure the air flow rate with a given accuracy. This helps to constrain the manufacturing cost of the inhaler into which the assembly 630 is incorporated.

Addition of the second pressure sensor 627 connected by a second conduit 629 (e.g., in some embodiments, having an internal diameter of approximately 2 mm and an internal length of approximately 9 mm), to the air flow path 614 at a position downstream of, and away from, the venturi section constriction 623 can assist in determining the air flow direction (i.e., to distinguish inhalation from exhalation). This allows a linked breath-actuation triggering mechanism (e.g., mechanical or electronic) to be arranged not to operate if the patient breathes out into the inhaler, rather than in through it, the two breathing modes being easily differentiated by the different relative pressure drop relationships detected by the first and second sensors 625 and 627.

In some embodiments, the first conduit 621 can have a first cross-sectional area (e.g., an average cross-sectional area, or a cross-sectional area in a region of the first conduit located adjacent the first pressure sensor); the second conduit 629 can have a second cross-sectional area (e.g., an average cross-sectional area, or a cross-sectional area in a region of the first conduit located adjacent the first pressure sensor); and the air flow path 614 can have a third cross-sectional area (e.g., an average cross-sectional area, or a cross-sectional area in a region of the first conduit or the second conduit).

In some embodiments, the ratio of the first cross-sectional area to the third cross-sectional area and/or the ratio of the second cross-sectional area to the third cross-sectional area can be no greater than 0.3; in some embodiments, no greater than 0.25; in some embodiments, no greater than 0.2; in some embodiments, no greater than 0.18; in some embodiments, no greater than 0.16; in some embodiments, no greater than 0.15; in some embodiments, no greater than 0.1; in some embodiments, no greater than 0.08; in some embodiments, no greater than 0.07; and in some embodiments, no greater than 0.05.

The present inventors calculated that, in some embodiments, an inhaler comprising the flow governor assembly 630 of FIG. 20 can provide an overall resistance to air flow at 20 L/min. (below the collapse flow rate) of around 0.8 $Pa^{0.5}$ min./L. This is a desirable figure for an inhaler for the treatment of either COPD or asthma. Computational Fluid Dynamics (CFD) is a useful tool for use by one skilled in the art to develop appropriately modified and dimensioned alternative embodiments to those shown herein.

In some embodiments, where an inhaler incorporates one or more pressure sensors, the patient's inhalation profile can be recorded for each use of the inhaler. With inclusion of the appropriate electronic components, e.g. a memory device and data transmission means, each inhalation profile of the patient can be captured, stored and retrieved for future analysis and interpretation. This can allow the patient's physician and others to monitor the patient's ability to use the inhaler successfully and can allow appropriate and timely health care advice and/or interventions to be provided.

Furthermore, in some embodiments, air flow pressure drop measurements can be made to enable an inhaler to register both the fact that a dose was taken and to record the corresponding inhalation profile. This enables the patient's physician, or an authority or organization paying for the patient's health care provision, to know that the patient has actually taken the dose. Previous inhalers that have registered the release of a dose, even with a record of the date and time of that release, have not registered or recorded the corresponding inhalation profile, making them vulnerable to 'dose dumping', a practice in which patients can deceive their physicians and others into thinking that they are taking their prescribed doses even when in fact they are simply wasting them by spraying the doses into the surrounding air, etc. Such practices are well known as occurring where patients are embarrassed to tell their physician that they have not been following their prescribed treatment regime. The ability to detect such practices, via utilization of embodiments of the present disclosure, allows health care professionals the opportunity to understand what patients are actually doing, and allows them to advise and/or alter treatment regimes accordingly.

Figure 21:
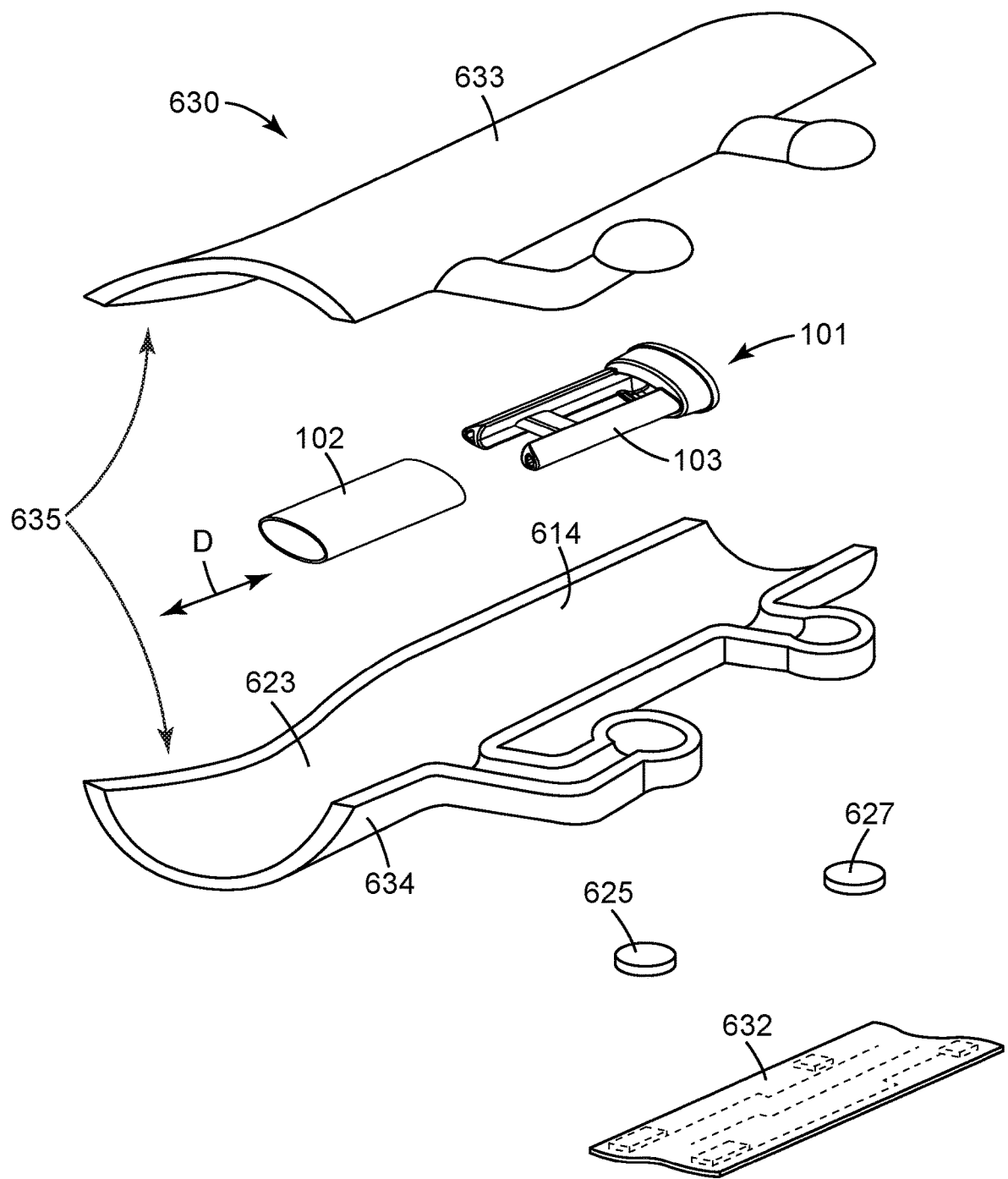
FIG. 21 is an exploded isometric view of the flow governor assembly of FIG. 20.

FIG. 21 illustrates one example of the elements or components that can be used to make the flow governor assembly 630 of FIG. 20. For example, in some embodiments, a controller 632 (e.g., a programmable circuit board (PCB)) can include the two pressure sensors 625, 627. As shown in FIGS. 20-21, the flow governor 101 comprises the tubular element 102 and the internal support structure 103. The air flow path 614 can be formed by a housing 635, which is shown as including a front housing 633 and a rear housing 634, e.g., for ease of plastic injection molding that can be coupled together (e.g., via any of the coupling means described above with respect to coupling the tubular element 102 and the internal support structure 103). In some embodiments, the housing 635 can be formed by two or more longitudinal portions (i.e., as shown in FIG. 21 by way of example), or additionally or alternatively, the housing 635 can be formed of two or more transverse portions that are joined transversely, relative to a longitudinal direction D, i.e., relative to the general air flow direction. The separate housing 635 is shown for simplicity and by way of example only; however, it should be understood that the assembly 630 and air flow path 614 can instead be formed (e.g., integrally formed) with a housing of a medicinal inhaler, and the inhaler can be modified to include all of the elements shown in FIGS. 20-21 of the assembly 630.

Various parameters affect the exact collapsing air flow rate and governing air flow rate for the flow governor 101 and the flow governor assembly 630. Examples of such parameters include the material forming the tubular element 102; the diameter and thickness of the tubular element material; the shape and dimensions of the constriction 623 and of the internal support structure 103; and environmental factors such as temperature and humidity (e.g., depending on the tubular element material). Based on the teachings of the present disclosure, a person of ordinary skill in the art will recognize how to test the effects of varying these different input parameters without departing from the spirit and scope of the present invention, in order to optimize an exact configuration of flow governor and air flow path for a particular application.

Figure 22:
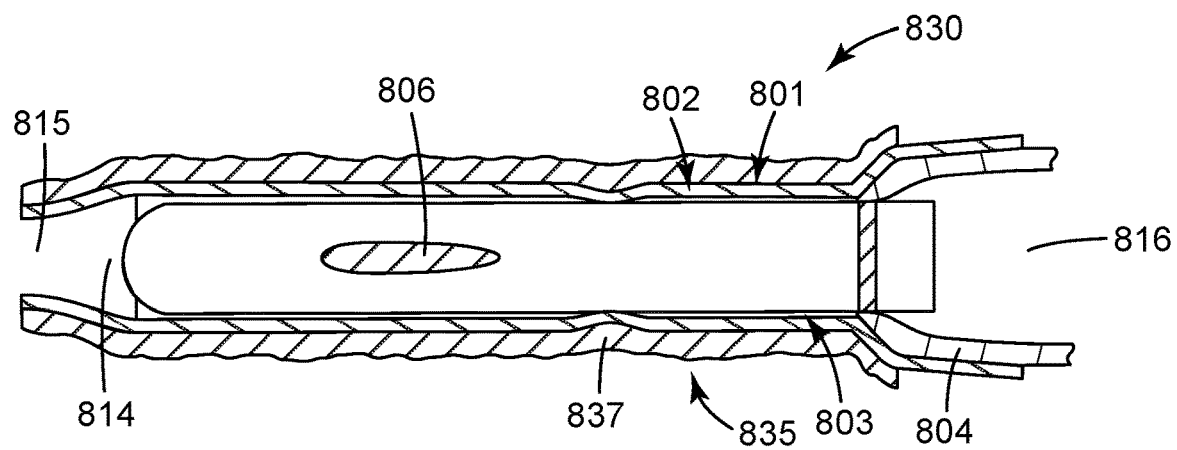
FIG. 22 is a side longitudinal cross-sectional view of a portion of a flow governor assembly of a medicinal inhaler according to another embodiment of the present disclosure, comprising a flow governor according to one embodiment of the present disclosure, shown at rest.

FIG. 22 illustrates a flow governor assembly 830 according to another embodiment of the present disclosure. The flow governor assembly 830 can be separately formed and put in fluid communication with or otherwise incorporated into an inhaler, or can form a portion of an inhaler of the present disclosure. As shown in FIG. 22, the flow governor assembly 830 can include a flow governor 801 positioned in an air flow path 814, the air flow path 814 including an air inlet 815 and an air outlet 816. The air flow path 814 can be formed by a housing 835. In some embodiments, the housing 835 can be a separate element that can be positioned within, positioned in fluid communication with, and/or coupled to a housing of an inhaler. Additionally, or alternatively, in some embodiments, the housing 835 can refer to a portion of a housing of an inhaler, such that the housing 835 is integrally formed with a housing of an inhaler.

The flow governor 801 includes a tubular element 802 and an internal support structure 803. As shown in FIG. 22 by way of example only, in some embodiments, the internal support structure 803 can include a hollow base 804 that can be at least partially formed by the housing 835, or a portion thereof, such that the tubular element 802 is stretched externally around one portion (e.g., an outer wall) of the housing 835 and is located internally with respect to another portion of the housing 835. In such embodiments, the entire internal support structure 803 can be integrally formed, or provided by, a portion of the housing 835, which, as described above, can also form at least a portion of an inhaler.

As further shown in FIG. 22, the air flow path 814 can include (e.g., the housing 835 can include) one or more inwardly-projecting protrusions or features 837 positioned at one or more desired longitudinal positions to encourage the tubular element 802 of the flow governor 801 to collapse at specific, pre-defined locations. In some embodiments, the one or inwardly-projecting protrusions 837 can be in the form of pinching splines, or in some embodiments, the protrusion(s) 837 can include an annular protrusion surrounding the tubular element 802. The protrusions(s) 837 can apply mechanical stress to the tubular element 802. By altering the size and/or number of the protrusion(s) 837, the flow rate at which the tubular element 802 collapses can be controlled. Additionally, or alternatively, in some embodiments, the tubular element material properties can be controlled to encourage precise collapse geometry and characteristics, e.g., by employing a particular Shore hardness at a specific section of the tubular element 802.

The protrusion(s) 837 can also reduce any tendency of the inwardly flexing regions of the tubular element 802 to stick to the housing 835, e.g. if the patient exhales moisture into the inhaler.

Furthermore, in some embodiments, the air flow path 814 can include a constriction, and particularly, a constriction located upstream of the flow governor 801, i.e., toward the air inlet 815, used as a venturi section to accelerate the local air velocity past an adjacent pressure sensor (not shown), as described above with respect to FIGS. 20 and 21. Such an arrangement can allow for more precise pressure measurements (and calculated air flow rate measurements) than would otherwise be achieved from a given pressure sensor.

Figure 23:
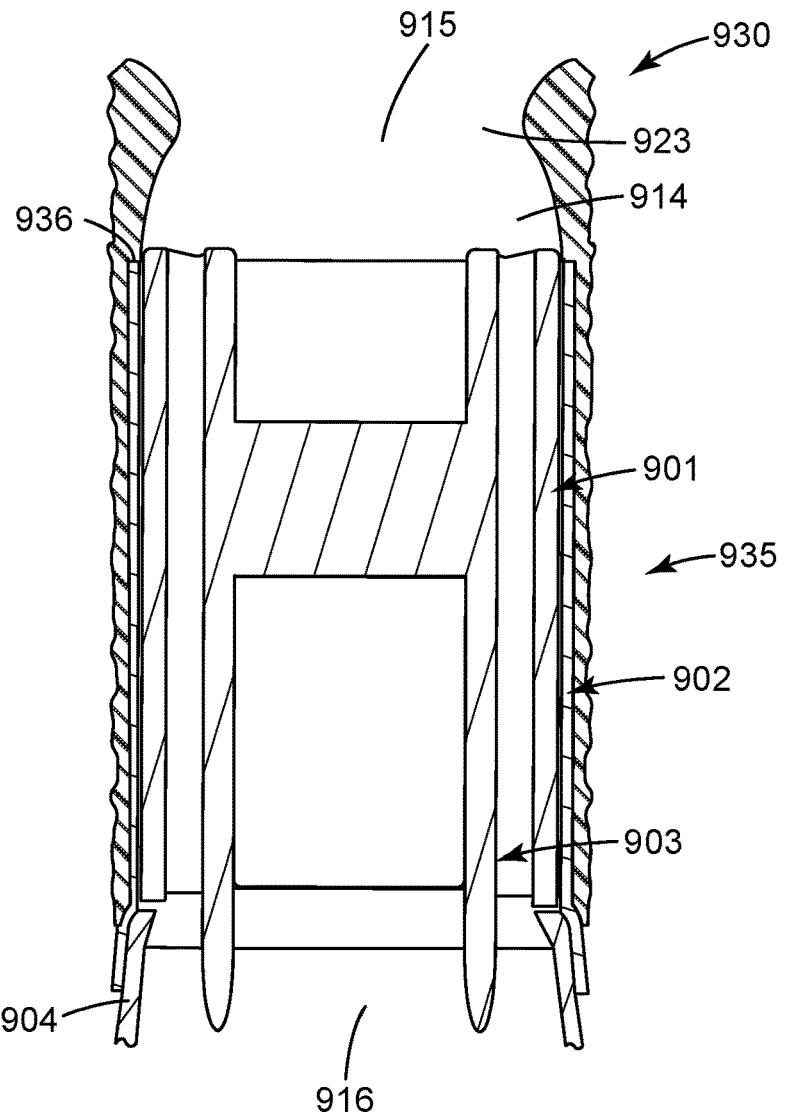
FIG. 23 is a front longitudinal cross-sectional view of a portion of a flow governor assembly of a medicinal inhaler according to another embodiment of the present disclosure, comprising a flow governor according to one embodiment of the present disclosure, shown at rest.

FIG. 23 illustrates a flow governor assembly 930 according to another embodiment of the present disclosure. The flow governor assembly 930 can be separately formed and put in fluid communication with or otherwise incorporated into an inhaler, or can form a portion of an inhaler of the present disclosure. As shown in FIG. 23, the flow governor assembly 930 can include a flow governor 901 positioned in an air flow path 914, the air flow path 914 including an air inlet 915 and an air outlet 916. The air flow path 914 can be formed by a housing 935. In some embodiments, the housing 935 can be a separate element that can be positioned within, positioned in fluid communication with, and/or coupled to a housing of an inhaler. Additionally, or alternatively, in some embodiments, the housing 935 can refer to a portion of a housing of an inhaler, such that the housing 935 is integrally formed with a housing of an inhaler.

The flow governor 901 includes a tubular element 902 and an internal support structure 903. As shown in FIG. 23 by way of example only, in some embodiments, the internal support structure 903 can include a hollow base 904 that can be at least partially formed by the housing 935, or a portion thereof, such that the tubular element 902 is stretched externally around one portion of the housing 935 and is located internally with respect to another portion of the housing 935. As shown, in some embodiments, the air flow path 914 can include a venturi constriction 923 upstream of the flow governor 901, which can be used to enhance the sensitivity of an adjacent pressure sensor (not shown) as has already been described.

In some embodiments, as shown in FIG. 23, the air flow path 914 can include one or more features that can be directly formed in the housing 935 into which the flow governor 901 sits to direct the flowing air into the flow governor 901. For example, as shown in FIG. 23, the air flow path 914 can include a channeling step 936 that directs the air flow into the flow governor 901 and prevents air flow to an outer, external, side of the tubular element 902, thus preventing pressure drop loss and keeping the air on the outer surface of the tubular element 902 stagnant.

Each embodiment shown in the figures is illustrated as a separate embodiment for clarity in illustrating a variety of features of the flow governors and medicinal inhalers of the present disclosure. However, it should be understood that any combination of elements and features of any of the embodiments illustrated in the figures and described herein can be employed in the flow governors and medicinal inhalers of the present disclosure. For example, any of the features of the flow governor assemblies of FIGS. 20-23, or combinations thereof, or partial combinations thereof, can be incorporated into any of the medicinal inhalers of FIGS. 15-19. Furthermore, any of the flow governor features of FIGS. 3-14, or combinations thereof, or partial combinations thereof, can be incorporated into any of the flow governor assemblies or medicinal inhalers of the present disclosure.

The following embodiments are intended to be illustrative of the present disclosure and not limiting.

Embodiments

First Set of Flow Governor Assembly Embodiments

1. A flow governor assembly for use with a medicinal inhaler, the assembly comprising:
   a housing;
   an air flow path defined by the housing and including an air inlet and an air outlet;
   a flow governor positioned in the air flow path (i.e., positioned in the housing) between the air inlet and the air outlet to govern air flow (e.g., substantially all of the air flow) in the air flow path to a target governing volumetric flow rate, the flow governor configured to provide a dynamic resistance to air flow in the air flow path as a function of air pressure drop between an inlet and an outlet of the flow governor; and
   a constriction in the air flow path (i.e., between the air inlet and the air outlet), the constriction configured to provide a static resistance to air flow in the air flow path, wherein the constriction is positioned in at least one of (i) a location in the housing upstream of the flow governor and (ii) a location in the housing downstream of the flow governor.

2. The assembly of embodiment 1, wherein the variable resistance and the static resistance are configured to provide an overall first resistance $R_1$ to air flow in the air flow path at a pressure drop of 0.5 kPa and an overall second resistance $R_2$ in the air flow path at a pressure drop of 4 kPa, wherein the ratio of $R_2/R_1$ is at least 1.5 (e.g., at a given volumetric flow rate).

3. The assembly of embodiment 1 or 2, wherein the ratio of $R_2/R_1$ is at least 2.

4. The assembly of any of embodiments 1-3, wherein the ratio of $R_2/R_1$ is no greater than 3.

5. The assembly of any of embodiments 1-4, wherein $R_1$ ranges from about 1.1 to about 0.4 $Pa^{0.5}$*min./L.

6. The assembly of any of embodiments 1-5, wherein $R_2$ ranges from about 3.2 to about 1.0 $Pa^{0.5}$*min./L.

7. The assembly of any of embodiments 1-6, wherein the constriction is configured to provide a static resistance to air flow of at least 0.4 $Pa^{0.5}$*min./L at a pressure drop between the air inlet and the air outlet of the air flow path of 0.5 kPa.

8. The assembly of any of embodiments 1-7, wherein the constriction is configured to provide a static resistance to air flow of no greater than 1.2 $Pa^{0.5}$*min./L at a pressure drop between the air inlet and the air outlet of the air flow path of 0.5 kPa.

9. The assembly of any of embodiments 1-8, wherein the constriction is configured to contribute to a total resistance to air flow of at least 1 $Pa^{0.5}$*min./L at a pressure drop between the air inlet and the air outlet of the air flow path of 4 kPa.

10. The assembly of any of embodiments 1-9, wherein the constriction is configured to contribute to a total resistance to air flow of no greater than 3.2 $Pa^{0.5}$*min./L at a pressure drop between the air inlet and the air outlet of the air flow path of 4 kPa.

11. The assembly of any of embodiments 1-10, wherein the target governing volumetric flow rate is at least about 25 L/min.

12. The assembly of any of embodiments 1-11, wherein the constriction is located upstream of the flow governor between the air inlet and the flow governor.

13. The assembly of any of embodiments 1-12, wherein the constriction includes at least one of a venturi section, a narrow passageway, and a tortuous path.

14. The assembly of any of embodiments 1-13, further comprising a channeling step formed in the housing to direct air flow into the flow governor and inhibit air flow in the air flow path from bypassing the flow governor.

15. The assembly of any of embodiments 1-14, further comprising a pressure sensor located in the air flow path upstream of the flow governor.

16. The assembly of embodiment 15, wherein the constriction is located upstream of the pressure sensor, between the air inlet and the pressure sensor.

17. The assembly of any of embodiments 1-16, further comprising a first pressure sensor located in the air flow path upstream of the flow governor and a second pressure sensor located in the air flow path downstream of the flow governor.

18. The assembly of embodiment 17, wherein the constriction is located upstream of the first pressure sensor in the air flow path, between the air inlet and the first pressure sensor.

19. The assembly of any of embodiments 1-18, further comprising a first pressure sensor located in a first conduit connected to the air flow path at a first location upstream of the flow governor and a second pressure sensor located in a second conduit connected to the air flow path at a second location downstream of the flow governor.

20. The assembly of embodiment 19, wherein the constriction is located adjacent the first location.

21. The assembly of embodiment 19, wherein the constriction is located upstream of the first location.

22. The assembly of any of embodiments 19-21, wherein the first conduit has a first cross-sectional area, the second conduit has a second cross-sectional area, and the air flow path has a third cross-sectional area, and wherein the ratio of the first cross-sectional area to the third cross-sectional area and the ratio of the second cross-sectional area to the third cross-sectional area are each no greater than 0.2.

23. The assembly of any of embodiments 1-22, wherein the flow governor assembly includes at least two flow governors positioned in the air flow path.

24. The assembly of embodiment 23, wherein the at least two flow governors are arranged in parallel.

25. The assembly of embodiment 23, wherein the at least two flow governors are arranged in series.

26. The assembly of any of embodiments 1-25, wherein the flow governor includes:
   a tubular element that defines at least a portion of an air flow path, the tubular element comprising at least one flexible wall configured to flex inwardly in response to an air flow in the air flow path; and
   an internal support structure, located within the tubular element and configured to preserve at least a predetermined cross-sectional area of the air flow path within the tubular element when the at least one flexible wall of the tubular element flexes inwardly.

27. The assembly of embodiment 26, wherein the wherein the internal support structure is rigid relative to the tubular element, and the tubular element is flexible relative to the internal support structure.

28. The assembly of embodiment 26 or 27, wherein the tubular element is substantially bistable between an uncollapsed state and a collapsed state.

29. The assembly of any of embodiments 26-28, wherein at least a portion of the internal support structure is formed by the housing.

30. The assembly of any of embodiments 1-29, wherein the housing forms at least a portion of a housing of a medicinal inhaler.

31. The assembly of any of embodiments 1-30, wherein the flow governor assembly is configured to be coupled to a housing of a medicinal inhaler.

32. The assembly of any of embodiments 1-31, wherein the flow governor assembly is configured to be positioned in fluid communication with an air flow path of a medicinal inhaler.

33. The assembly of any of embodiments 1-32, wherein the air inlet of the air flow path is the air inlet of a medicinal inhaler.

34. A medicinal inhaler comprising:
   an air flow path including an aspiration orifice and an inhalation orifice; and
   the flow governor assembly of any of the preceding embodiments positioned in fluid communication with the air flow path of the inhaler (e.g., such that the assembly is positioned between the aspiration orifice and the inhalation orifice of the inhaler).

Second Set of Flow Governor Assembly Embodiments

1. A flow governor assembly for use with a medicinal inhaler, the assembly comprising:
   a housing;
   an air flow path defined by the housing and including an air inlet and an air outlet;
   a flow governor positioned in the air flow path (i.e., positioned in the housing) between the air inlet and the air outlet to govern air flow (e.g., substantially all of the air flow) in the air flow path to a target governing volumetric flow rate, the flow governor configured to provide a variable resistance to air flow in the air flow path as a function of air pressure drop between an inlet and an outlet of the flow governor;
   a first pressure sensor located in the air flow path (e.g., positioned in the housing) upstream of the flow governor; and a second pressure sensor located in the air flow path (e.g., positioned in the housing) downstream of the flow governor.

2. The assembly of embodiment 1, further comprising a constriction located upstream of the first pressure sensor in the air flow path, between the air inlet and the first pressure sensor.

3. The assembly of embodiment 2, wherein the constriction includes at least one of a venturi section, a narrow passageway, and a tortuous path.

4. The assembly of any of embodiments 1-3, wherein the first pressure sensor is located in a first conduit connected to the air flow path at a first location upstream of the flow governor, wherein the second pressure sensor is located in a second conduit connected to the air flow path at a second location downstream of the flow governor.

5. The assembly of embodiment 4, further comprising a constriction located adjacent the first location.

6. The assembly of embodiment 4, further comprising a constriction located upstream of the first location.

7. The assembly of any of embodiments 4-7, wherein the first conduit has a first cross-sectional area, the second conduit has a second cross-sectional area, and the air flow path has a third cross-sectional area, and wherein the ratio of the first cross-sectional area to the third cross-sectional area and the ratio of the second cross-sectional area to the third cross-sectional area are each no greater than 0.2.

8. The assembly of any of embodiments 1-7, wherein the flow governor assembly includes at least two flow governors positioned in the air flow path.

9. The assembly of embodiment 8, wherein the at least two flow governors are arranged in parallel.

10. The assembly of embodiment 8, wherein the at least two flow governors are arranged in series.

11. The assembly of any of embodiments 1-10, wherein the flow governor includes:
   a tubular element that defines at least a portion of an air flow path, the tubular element comprising at least one flexible wall configured to flex inwardly in response to an air flow in the air flow path; and
   an internal support structure, located within the tubular element and configured to preserve at least a predetermined cross-sectional area of the air flow path within the tubular element when the at least one flexible wall of the tubular element flexes inwardly.

12. The assembly of embodiment 11, wherein the wherein the internal support structure is rigid relative to the tubular element, and the tubular element is flexible relative to the internal support structure.

13. The assembly of embodiment 11 or 12, wherein the tubular element is substantially bistable between an uncollapsed state and a collapsed state.

14. The assembly of any of embodiments 11-13, wherein at least a portion of the internal support structure is formed by the housing.

15. The assembly of any of embodiments 1-14, wherein the housing forms at least a portion of a housing of a medicinal inhaler.

16. The assembly of any of embodiments 1-15, wherein the flow governor assembly is configured to be coupled to a housing of a medicinal inhaler.

17. The assembly of any of embodiments 1-16, wherein the flow governor assembly is configured to be positioned in fluid communication with an air flow path of a medicinal inhaler.

18. The assembly of any of embodiments 1-17, wherein the air inlet of the air flow path is the air inlet of a medicinal inhaler.

19. A medicinal inhaler comprising:
   an air flow path including an aspiration orifice and an inhalation orifice; and
   the flow governor assembly of any of the preceding embodiments positioned in fluid communication with the air flow path of the inhaler (e.g., such that the assembly is positioned between the aspiration orifice and the inhalation orifice of the inhaler).

20. The inhaler of embodiment 19, wherein the first pressure sensor and the second pressure sensor are positioned to sense the inspiratory air flow rate and direction through the flow governor assembly.

Flow Governor Embodiments

1. A flow governor for use in a medicinal inhaler, the flow governor comprising:

a tubular element that defines at least a portion of an air flow path, the tubular element comprising at least one flexible wall configured to flex inwardly in response to an air flow in the air flow path; and an internal support structure, located within the tubular element and configured to preserve at least a predetermined cross-sectional area of the air flow path within the tubular element when the at least one flexible wall of the tubular element flexes inwardly.

2. The flow governor of embodiment 1, wherein the flow governor is substantially linear.

3. The flow governor of embodiment 1 or 2, wherein the tubular element is substantially bistable between an uncollapsed state and a collapsed state.

4. The flow governor of any of embodiments 1-3, wherein the internal support structure is rigid relative to the tubular element, and the tubular element is flexible relative to the internal support structure.

5. The flow governor of any of embodiments 1-4, further comprising a longitudinal direction, wherein the at least one flexible wall of the tubular element is oriented substantially parallel to the longitudinal direction.

6. The flow governor of embodiment 5, wherein the tubular element is elongated along in the longitudinal direction.

7. The flow governor of any of embodiments 1-6, further comprising:
an air inlet located at a first end of the tubular element; and
an air outlet located at a second end, opposite the first end, of the tubular element.

8. The flow governor of any of embodiments 1-7, wherein the flow governor has an elliptical transverse cross-sectional shape.

9. The flow governor of any of embodiments 1-8, wherein the tubular element has an elliptical transverse cross-sectional shape.

10. The flow governor of any of embodiments 1-9, wherein the internal support structure has a base having an outer wall, and wherein an end of the tubular element is stretched over the outer wall of the base of the internal support structure.

11. The flow governor of embodiment 10, wherein the outer wall of the base of the internal support structure has an elliptical transverse cross-sectional shape.

12. The flow governor of embodiment 10 or 11, wherein the outer wall of the base of the internal support structure has a circular transverse cross-sectional shape.

13. The flow governor of any of embodiments 1-12, wherein the internal support structure includes at least one hollow pillar, and wherein the air flow path through the flow governor includes a space between an outer wall of the internal support structure and the tubular element, and a space within the at least one hollow pillar.

14. The flow governor of any of embodiments 1-13, wherein the internal support structure has a generally H-shaped transverse cross-sectional shape.

15. The flow governor of any of embodiments 1-14, wherein the internal support structure has a generally H-shaped longitudinal cross-sectional shape.

16. The flow governor of any of embodiments 1-15, wherein the internal support structure includes a transverse cross-sectional shape comprising at least one capital English letter "E".

17. The flow governor of any of embodiments 1-16, wherein the internal support structure includes a transverse cross-sectional shape comprising at least one of the capital English letters selected from B, C, D, E, H, M, N, O, S, V, W, X and Z.

18. The flow governor of any of embodiments 1-17, wherein the internal support structure includes at least one pillar oriented substantially along a longitudinal direction of the tubular element and protruding from an inlet end of the tubular element.

19. The flow governor of any of embodiments 1-18, wherein the internal support structure includes at least one hollow pillar defining a lumen therein.

20. The flow governor of any of embodiments 1-19, wherein the internal support structure includes at least one solid pillar.

21. The flow governor of any of embodiments 1-20, wherein the internal support structure includes two pillars oriented substantially parallel to a longitudinal direction of the tubular element, and a cross member positioned to couple the two pillars, the cross member oriented at a non-zero angle with respect to the longitudinal direction.

22. The flow governor of any of embodiments 1-21, wherein the internal support structure includes two hollow pillars oriented substantially parallel to a longitudinal direction of the tubular element, each pillar defining a lumen therein, and a solid cross member positioned to couple the two hollow pillars, the cross member oriented at a non-zero angle with respect to the longitudinal direction.

23. The flow governor of any of embodiments 1-21, wherein the internal support structure includes two solid pillars oriented substantially parallel to a longitudinal direction of the tubular element, and a solid cross member positioned to couple the two solid pillars, the cross member oriented at a non-zero angle with respect to the longitudinal direction.

24. The flow governor of any of embodiments 21, 22 and 23, wherein the internal support structure includes at least one transverse protrusion extending from the cross member.

25. The flow governor of any of embodiments 21-24, wherein the cross member is oriented substantially perpendicularly with respect to the longitudinal direction.

26. The flow governor of any of embodiments 1-25, wherein the internal support structure includes at least one rib that protrudes substantially orthogonally with respect to the at least one flexible wall of the tubular element.

27. A medicinal inhaler comprising at least one flow governor of any of the preceding embodiments positioned in fluid communication with an air flow path of the medicinal inhaler.

28. The medicinal inhaler of embodiment 27, wherein the medicinal inhaler includes at least two flow governors arranged in parallel.

29. The medicinal inhaler of embodiment 27 or 28, wherein the medicinal inhaler includes at least two flow governors arranged in series.

30. A medicinal inhaler comprising:
a housing comprising
a tubular sleeve portion dimensioned to receive a canister comprising a medicament, and
a patient port;
an air flow path including an air inlet and an air outlet, wherein the air outlet is defined by the patient port; and
the flow governor of any of embodiments 1-26 positioned in the air flow path.

31. The medicinal inhaler of any of embodiments 27-30, wherein the medicinal inhaler is a pressurized metered dose inhaler (pMDI).

32. The medicinal inhaler of any of embodiments 27-30, wherein the medicinal inhaler is at least one of a breath-actuated inhaler, a pressurized metered dose inhaler (pMDI), a dry powder inhaler (DPI), a nebulizer, and a combination thereof.

33. The medicinal inhaler of any of embodiments 30-32, wherein the tubular sleeve portion of the housing includes a first open end, and wherein the housing further includes a second open end dimensioned to receive the flow governor.

34. The medicinal inhaler of embodiment 33, wherein the housing further includes a cover or a seal positioned to seal the first open end from ambience.

35. The medicinal inhaler of any of embodiments 27-34, wherein the flow governor is positioned in a dedicated air flow path, wherein the dedicated air flow path includes an air inlet open to ambience and an air outlet in fluid communication with the air flow path of the inhaler, and wherein the flow governor is positioned between the air inlet and the air outlet of the dedicated air flow path.

36. The medicinal inhaler of embodiment 35, wherein the dedicated air flow path is integrally formed with the housing.

37. The medicinal inhaler of embodiment 35, or 36, wherein the dedicated air flow path is formed in a rear portion of the housing, opposite the patient port.

38. The medicinal inhaler of embodiment 35 or 36, wherein the dedicated air flow path is formed in a bottom portion of the housing.

39. The medicinal inhaler of embodiment 38, wherein the air inlet of the dedicated air flow path is located below the patient port.

40. The medicinal inhaler of any of embodiments 30-39, further comprising a cover positioned over the tubular sleeve portion of the housing to seal the open end from ambience, such that any air taken into the inhaler is moved through the flow governor.

41. The medicinal inhaler of any of embodiments 30-40, further comprising a skirt seal located between an outer surface of the canister and an inner surface of the housing.

42. The medicinal inhaler of any of embodiments 30-41, further comprising a cap configured to be coupled to the tubular sleeve portion of the housing to seal the tubular sleeve portion, the cap defining the air inlet and including the flow governor.

43. The medicinal inhaler of any of embodiments 27-42, further comprising a pressure sensor located in the air flow path upstream of the flow governor.

44. The medicinal inhaler of any of embodiments 27-43, further comprising a first pressure sensor located in the air flow path upstream of the flow governor and a second pressure sensor located in the air flow path downstream of the flow governor.

45. A flow governor assembly for use in a medicinal inhaler, the flow governor assembly comprising:
a housing;
an air flow path defined by the housing and including an air inlet and an air outlet; and
the flow governor of any of embodiments 1-26, the flow governor being positioned in the air flow path between the air inlet and the air outlet.

46. The flow governor assembly of embodiment 45, further comprising a first pressure sensor positioned in fluid communication with the air flow path upstream of the flow governor and a second pressure sensor positioned in fluid communication with the air flow path downstream of the flow governor.

47. The flow governor assembly of embodiment 45 or 46, further comprising a first pressure sensor located in a first conduit connected to the air flow path upstream of the flow governor and a second pressure sensor located in a second conduit connected to the air flow path downstream of the flow governor.

48. The air flow path of embodiment 47, further comprising a constriction located in the air flow path adjacent where the first conduit connects to the air flow path.

49. The air flow path of any of embodiments 45-48, further comprising a constriction located between the air inlet and the flow governor.

50. A method of using a medicinal inhaler, the method comprising:
providing a medicinal inhaler comprising a flow governor according to any of embodiments 1-26; and
varying an air flow resistance of the inhaler in response to air flow in the air flow path of the flow governor.

51. The method of embodiment 50, further comprising inserting a patient port of the medicinal inhaler into a body cavity of a patient; and inhaling through the patient port to cause air flow in the air flow path of the flow governor.

52. The method of embodiment 50 or 51, wherein varying the air flow resistance of the inhaler includes flexing the at least one tubular wall inwardly toward the internal support structure.

It is to be understood that the invention is not limited in its application to the details of construction and the arrangement of components set forth in the above description or illustrated in the accompanying drawings. The invention is capable of other embodiments and of being practiced or of being carried out in various ways. Also, it is to be understood that the phraseology and terminology used herein is for the purpose of description and should not be regarded as limiting. It is to be further understood that other embodiments may be utilized, and structural or logical changes may be made without departing from the scope of the present disclosure.

The following prophetic examples are intended to be illustrative of the present disclosure and not limiting.

EXAMPLES

Example 1—Governing Flow Rate

Figure 24:
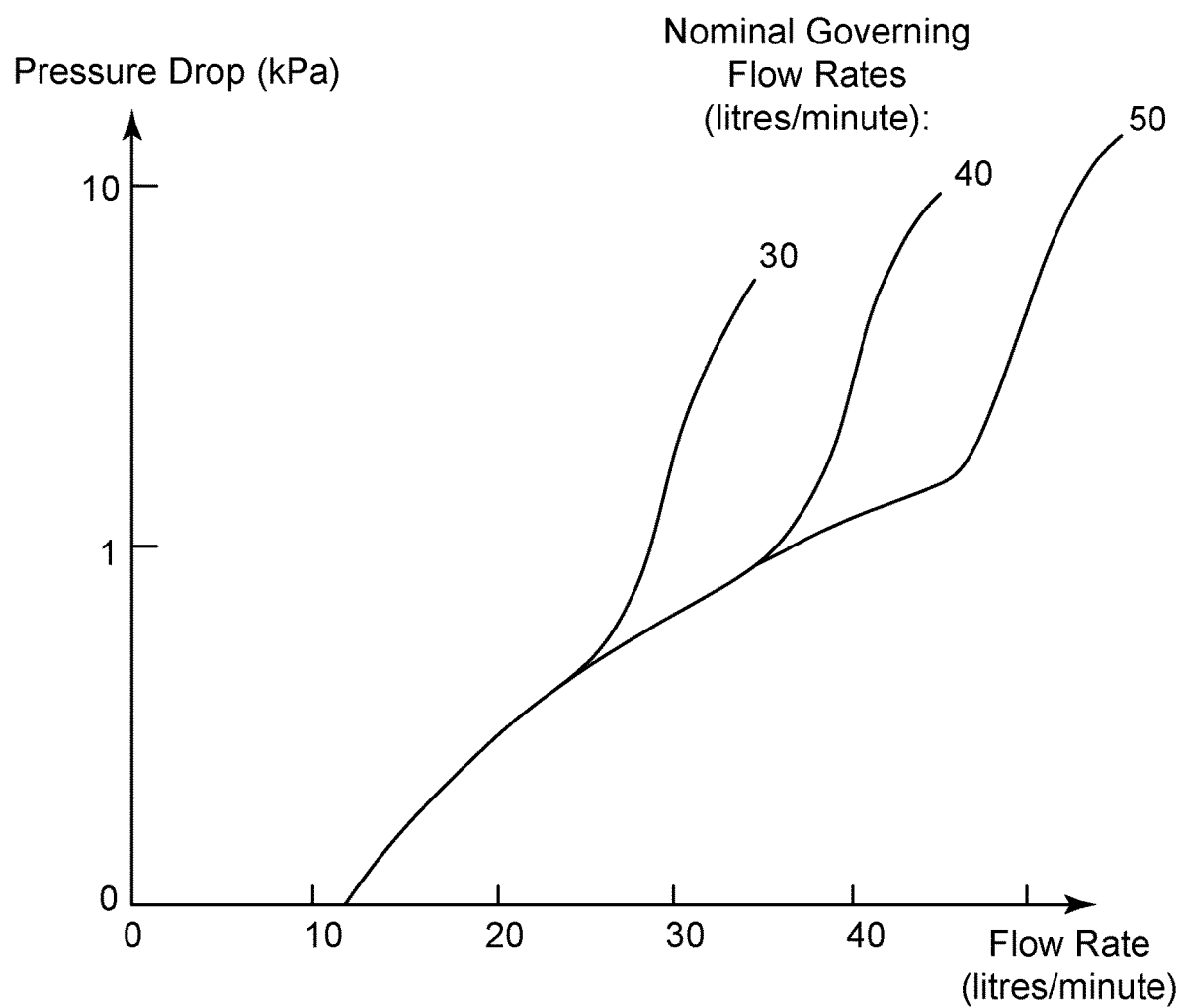
FIG. 24 is a graph of inhalation pressure drop (kPa) versus inhalation flow rate (L/min.) for three different embodiments of flow governors of the present disclosure.

FIG. 24 and Table 1 show the calculated range of flowrates that patients will inhale through flow governor assemblies having the configuration of the flow governor assembly 630 of FIGS. 20 and 21, comprising the flow governor 101 of FIGS. 3-8, with nominal flow governing values of 30, 40 and 50 L/min., respectively. It is clear from FIG. 24 and Table 1 that the spread in flow rates is greater for the higher flow governor nominal governing flow rates.

For modeling purposes, a normal distribution of governing flowrates has been taken around each target governing volumetric flow rate (i.e., 30 L/min., 40 L/min. and 50 L/min.), and the below spreads of data represent the distributions of flow rates at which the flow governors will operate within a population of flow governor assemblies. For example, for the case of a target governing volumetric flow rate of 30 L/min., a small number of flow governors will collapse at around 25 L/min, whereas most would be expected to govern at a flow rate close to the target of 30 L/min, and a small number will govern at a flow rate close to 35 L/min. It is assumed that if a flow governor collapses, then the resistance to flow will increase significantly and the pressure drop will be dominated by the dynamic, or variable, resistance.

The below data were calculated by modeling the pressure drop at various flow rates using the following equation:

$$\text{Pressure drop}(Pa) = ((R^2 + D^2) \times F^2)/1000$$

where: R=Static resistance, $Pa^{0.5}$(min./L)
D=Dynamic resistance, $Pa^{0.5}$(min./L)
F=Flow rate, L/min The static resistance of the flow governor assembly 630 was estimated to be 0.83 $Pa^{0.5}$(min./L), based on a combination of the resistance from the inlet losses, venturi resistance, the resistance of the flow governor, and the outlet losses.

TABLE 1

Ranges of flowrates with governing flow rates of 30, 40 and 50 L/min.

| Nominal governing flow rate | Flow rate when inhaling at 0.5 kPa | Flow rate when inhaling at 4 kPa |
|---|---|---|
| 30 L/min. | 25 L/min. | 35 L/min. |
| 40 L/min. | 27 L/min. | 45 L/min. |
| 50 L/min. | 27 L/min. | 55 L/min. |

The inventors have found particular advantages with flow governors of this configuration having a nominal governing flow rate of 30 L/min.

Example 2—Air Flow Resistance

Another important parameter that can be optimized is the static air flow resistance of the assembly.

A flow governor assembly having the configuration of the flow governor assembly 630 of FIGS. 20-21, comprising the flow governor 101 of FIGS. 3-8 was formed having a static resistance of 0.83 $Pa^{0.5}$ (min./L) and a nominal governing flow rate of 30 L/min. The performance of such a flow governor assembly is illustrated by the solid trace in FIG. 25, derived from data calculated using the equation described above in Example 1. As shown, this design of flow governor assembly will allow a patient who inhales with a pressure drop of only 0.5 kPa to inhale through the assembly at 25 L/min. The other extreme is a patient who creates a pressure drop of 4 kPa, and in this circumstance the inhalation flow rate will be governed according to the tolerance of the flow governor to between approximately 25 and 35 L/min. As is clear from the solid trace, this design ensures that all medications will be delivered within this flow rate range of approximately 25 to 35 L/min., independent of patient lung capacity. This will substantially improve dose consistency for patients (e.g., COPD patients), both inter-patient and intra-patient. All patients will thus benefit from such a flow governor assembly.

Figure 25:
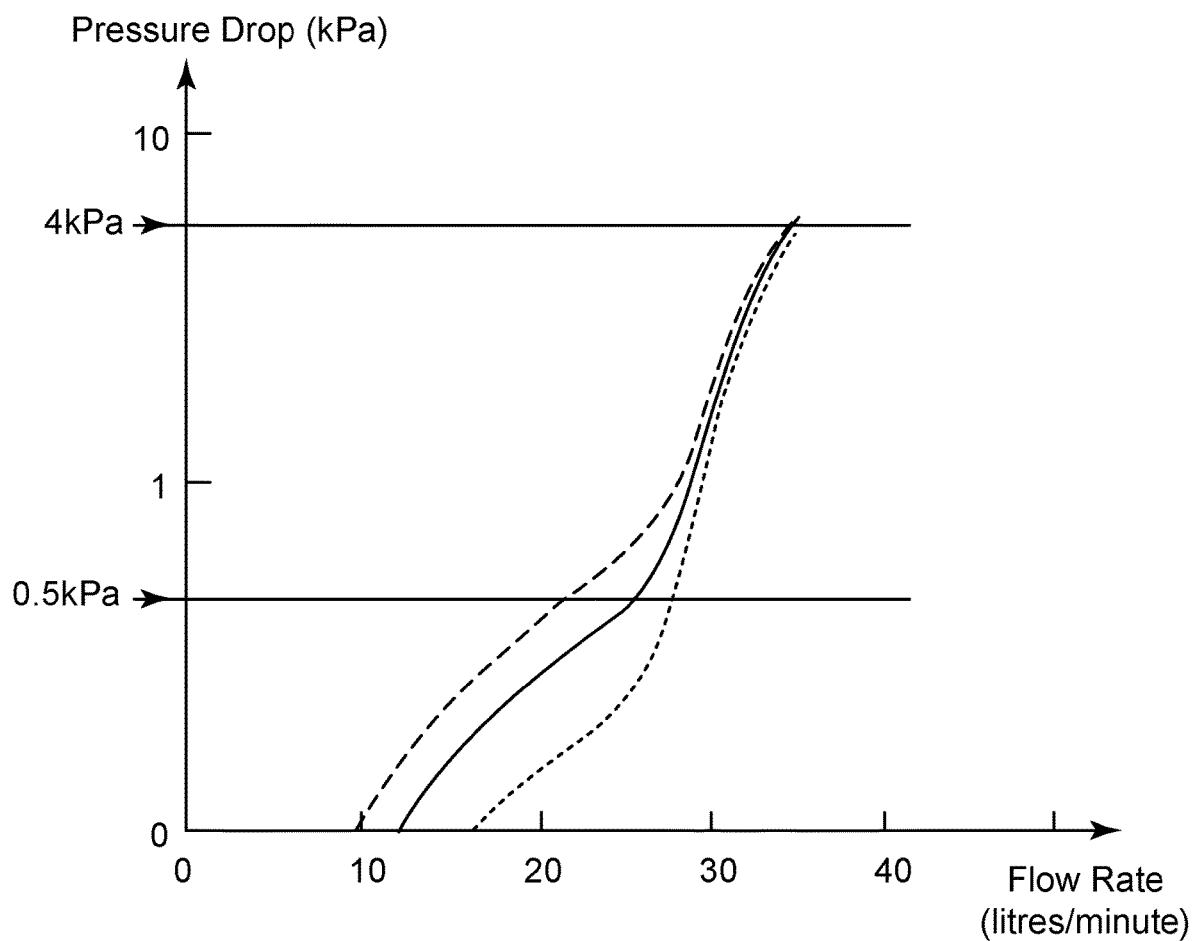
FIG. 25 is a graph of inhalation pressure drop (kPa) versus inhalation flow rate (L/min.) for three further embodiments of flow governors of the present disclosure.

The dashed trace in FIG. 25 shows the effect of a higher static resistance for the assembly, of 1.0 $Pa^{0.5}$ min./L. Some patients, particularly those who inhale with a pressure drop of only around 0.5 kPa, will not achieve the flow rate required for the flow governor to operate. These patients will not benefit directly from the flow governor.

The dotted trace in FIG. 25 shows the effect of a lower static resistance for the flow governor assembly, of 0.6 $Pa^{0.5}$ min./L. All patients will find it easier to inhale through the assembly and some weaker patients will find it easier to obtain a flow rate close to the governing flow rate. However, too low a static resistance can lead to increased drug deposition in the mouth and the throat, which is undesirable, so it is also preferable to avoid the static resistance being too low.

TABLE 2

| Characteristics | Flow rate when inhaling at 0.5 kPa | Flow rate when inhaling at 4 kPa |
|---|---|---|
| 30 L/min. flow governor; 0.6 $Pa^{0.5}$ min./L static resistance | 28 L/min. | 35 L/min. |
| 30 L/min. flow governor; 0.8 $Pa^{0.5}$ min./L static resistance | 25 L/min. | 35 L/min. |
| 30 L/min. flow governor; 1.0 $Pa^{0.5}$ min./L static resistance | 22 L/min. | 34 L/min. |

On the basis of these calculations and these considerations, the ideal static resistance for the flow governor assembly of FIGS. 20-21 comprising the flow governor of FIGS. 3-8 with a governing flow rate of 30 L/min. is considered to be around 0.8 $Pa^{0.5}$ min./L. At this resistance, practically all COPD and asthma patients would be expected to inhale at a flowrate above about 30 L/min. A higher resistance (e.g. 1.0-1.1 $Pa^{0.5}$ min./L) assembly, would result in some COPD patients not being able to reach an inhalation rate of 30 L/min.

Typically, only 95% of COPD patients produce an inhalation pressure drop of greater than 0.6 kPa. As a result, provision of flow governor assemblies (and/or inhalers) comprising the flow governors of the present disclosure caters satisfactorily for the vast majority of asthma and COPD patients, who can produce an inhalation pressure drop of between 0.5 and 4.0 kPa.

The embodiments described above and illustrated in the figures are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure.

All references and publications cited herein are expressly incorporated herein by reference in their entirety into this disclosure.

Various features and aspects of the present disclosure are set forth in the following claims.

What is claimed is:

1. A flow governor assembly for use with a medicinal inhaler, the assembly comprising:
a housing;
an air flow path defined by the housing and including an air inlet and an air outlet;
a flow governor positioned in the air flow path between the air inlet and the air outlet to govern air flow in the air flow path to a target governing volumetric flow rate, the flow governor configured to provide a dynamic resistance to air flow in the air flow path as a function of air pressure drop between an inlet and an outlet of the flow governor;
a first pressure sensor and a second sensor;
a constriction in the air flow path located between the air inlet and the air outlet and comprising a venturi section, the constriction configured to provide a static resistance to air flow in the air flow path, wherein the venturi section is positioned upstream of the flow governor and adjacent the first pressure sensor to sense the pressure through the venturi section; and
wherein the second pressure sensor is located downstream the flow governor.

2. The assembly of claim 1, wherein the variable resistance and the static resistance are configured to provide an overall first resistance $R_1$ to air flow in the air flow path at a pressure drop of 0.5 kPa and an overall second resistance $R_2$ in the air flow path at a pressure drop of 4 kPa, wherein the ratio of $R_2/R_1$ is at least 1.5.

3. The assembly of claim 1, wherein the constriction is configured to provide a static resistance to air flow of at least 0.4 $Pa^{0.5}$*min./L at a pressure drop between the air inlet and the air outlet of the air flow path of 0.5 kPa.

4. The assembly of claim 1, wherein the constriction is configured to provide a static resistance to air flow of no greater than 1.2 $Pa^{0.5}$*min./L at a pressure drop between the air inlet and the air outlet of the air flow path of 0.5 kPa.

5. The assembly of claim 1, wherein the constriction is configured to contribute to a total resistance to air flow of at least 1 $Pa^{0.5}$*min./L at a pressure drop between the air inlet and the air outlet of the air flow path of 4 kPa.

6. The assembly of claim 1, wherein the constriction is configured to contribute to a total resistance to air flow of no greater than 3.2 $Pa^{0.5}$*min./L at a pressure drop between the air inlet and the air outlet of the air flow path of 4 kPa.

7. The assembly of claim 1, wherein the target governing volumetric flow rate is at least about 25 L/min.

8. The assembly of claim 1, wherein the constriction further includes at least one of a narrow passageway or a tortuous path.

9. The assembly of claim 1, further comprising a channeling step formed in the housing to direct air flow into the flow governor and inhibit air flow in the air flow path from bypassing the flow governor.

10. The assembly of claim 1, wherein the first pressure sensor is located in a first conduit connected to the air flow path at a first location upstream of the flow governor and the second pressure sensor is located in a second conduit connected to the air flow path at a second location downstream of the flow governor.

11. The assembly of claim 10, wherein the first conduit has a first cross-sectional area, the second conduit has a second cross-sectional area, and the air flow path has a third cross-sectional area, and wherein the ratio of the first cross-sectional area to the third cross-sectional area and the ratio of the second cross-sectional area to the third cross-sectional area are each no greater than 0.2.

12. The assembly of claim 1, wherein the flow governor includes:
 a tubular element that defines at least a portion of an air flow path, the tubular element comprising at least one flexible wall configured to flex inwardly in response to an air flow in the air flow path; and
 an internal support structure, located within the tubular element and configured to preserve at least a predetermined cross-sectional area of the air flow path within the tubular element when the at least one flexible wall of the tubular element flexes inwardly.

13. The assembly of claim 12, wherein the internal support structure is rigid relative to the tubular element, and the tubular element is flexible relative to the internal support structure.

14. The assembly of claim 12, wherein at least a portion of the internal support structure is formed by the housing.

15. The assembly of claim 1, wherein the housing forms at least a portion of a housing of a medicinal inhaler.

16. The assembly of claim 1, wherein the flow governor assembly is configured to be coupled to a housing of a medicinal inhaler.

17. The assembly of claim 1, wherein the flow governor assembly is configured to be positioned in fluid communication with an air flow path of a medicinal inhaler.

18. A medicinal inhaler comprising:
 an air flow path including an aspiration orifice and an inhalation orifice; and
 the flow governor assembly of claim 1 positioned in fluid communication with the air flow path of the inhaler.

\* \* \* \* \*